(12) United States Patent
Bochenko et al.

(10) Patent No.: US 9,078,809 B2
(45) Date of Patent: Jul. 14, 2015

(54) MEDICATION DOSE PREPARATION AND TRANSFER SYSTEM

(75) Inventors: Walter John Bochenko, Encinitas, CA (US); Stephen M. Prince, La Jolla, CA (US); Christopher Biagioli, La Jolla, CA (US)

(73) Assignee: CRISI Medical Systems, Inc., San Diego, CA (US)

( * ) Notice: Subject to any disclaimer, the term of this patent is extended or adjusted under 35 U.S.C. 154(b) by 343 days.

(21) Appl. No.: 13/524,736

(22) Filed: Jun. 15, 2012

(65) Prior Publication Data

US 2012/0323208 A1    Dec. 20, 2012

Related U.S. Application Data

(60) Provisional application No. 61/497,855, filed on Jun. 16, 2011.

(51) Int. Cl.
*A61B 19/00* (2006.01)
*A61M 5/32* (2006.01)
*A61J 1/20* (2006.01)
(Continued)

(52) U.S. Cl.
CPC .............. *A61J 1/2096* (2013.01); *A61J 1/1412* (2013.01); *A61J 1/22* (2013.01); *A61J 2001/201* (2013.01); *A61J 2001/2037* (2013.01); *A61J 2001/2062* (2013.01); *A61J 2205/10* (2013.01); *A61J 2205/60* (2013.01); *A61M 5/1782* (2013.01); *A61M 2205/6009* (2013.01); *A61M 2205/6036* (2013.01); *A61M 2205/6054* (2013.01); *G06F 19/3468* (2013.01)

(58) Field of Classification Search
CPC ..... A61J 2205/10; A61J 2200/70; A61J 1/20; A61J 1/2089; A61J 1/2093; A61J 1/2096; A61J 2001/2003; A61J 2001/202; A61J 2001/2065; A61J 2205/00; A61J 2205/60; G06F 19/3468; G06K 7/00; G06K 7/10; G06K 19/00; G06K 19/005
USPC .................................................. 604/411–415
See application file for complete search history.

(56) References Cited

U.S. PATENT DOCUMENTS 4,650,475 A    3/1987    Smith et al.
4,853,521 A    8/1989    Claeys et al.
(Continued)

FOREIGN PATENT DOCUMENTS

DE    29617777 U1    12/1996
EP    1980974 A2    10/2008

OTHER PUBLICATIONS

International Search Report dated Aug. 2, 2011 for corresponding PCT Application No. PCT/US2010/055322.
(Continued)

*Primary Examiner* — Leslie Deak
*Assistant Examiner* — Kai Weng
(74) *Attorney, Agent, or Firm* — The Webb Law Firm

(57) ABSTRACT

Apparatus, systems, methods and articles are described to prepare and track medications and medication containers as they are prepared, administered to patients and, in some cases, disposed of. Information such as medication type, concentration, and volume are associated with medication containers during preparation and this information can later be consumed/utilized when administering the medication from a container to a patient. Disposing of any remaining medication can also be tracked.

32 Claims, 14 Drawing Sheets

(51) Int. Cl.
*A61J 1/14* (2006.01)
*A61J 1/22* (2006.01)
*A61M 5/178* (2006.01)
*G06F 19/00* (2011.01)

(56) References Cited

U.S. PATENT DOCUMENTS

| | | | |
|---|---|---|---|
| 4,978,335 A | 12/1990 | Arthur, III | |
| 5,011,032 A | 4/1991 | Rollman | |
| 5,078,683 A | 1/1992 | Sancoff et al. | |
| 5,279,576 A | 1/1994 | Loo et al. | |
| 5,338,157 A | 8/1994 | Blomquist | |
| 5,383,858 A | 1/1995 | Reilly et al. | |
| 5,628,309 A | 5/1997 | Brown | |
| 5,651,775 A | 7/1997 | Walker et al. | |
| 5,692,640 A | 12/1997 | Caulfield et al. | |
| 5,713,856 A | 2/1998 | Eggers et al. | |
| 5,781,442 A | 7/1998 | Engleson et al. | |
| 5,782,814 A | 7/1998 | Brown et al. | |
| 5,792,117 A | 8/1998 | Brown | |
| 5,873,731 A | 2/1999 | Prendergast | |
| 5,920,263 A | 7/1999 | Huttenhoff et al. | |
| 5,941,846 A | 8/1999 | Duffy et al. | |
| 5,984,901 A | 11/1999 | Sudo et al. | |
| 6,019,745 A | 2/2000 | Gray | |
| 6,039,251 A | 3/2000 | Holowko et al. | |
| 6,123,686 A | 9/2000 | Olsen et al. | |
| 6,192,945 B1 | 2/2001 | Ford et al. | |
| 6,270,455 B1 | 8/2001 | Brown | |
| 6,277,099 B1 * | 8/2001 | Strowe et al. | 604/207 |
| 6,338,200 B1 | 1/2002 | Baxa et al. | |
| 6,468,424 B1 | 10/2002 | Donig et al. | |
| 6,471,089 B2 | 10/2002 | Liff et al. | |
| 6,579,231 B1 | 6/2003 | Phipps | |
| RE38,189 E | 7/2003 | Walker et al. | |
| 6,626,862 B1 | 9/2003 | Duchon et al. | |
| D481,121 S | 10/2003 | Evans | |
| 6,671,563 B1 | 12/2003 | Engelson et al. | |
| D485,356 S | 1/2004 | Evans | |
| 6,685,678 B2 | 2/2004 | Evans et al. | |
| 6,731,989 B2 | 5/2004 | Engleson et al. | |
| 6,790,198 B1 | 9/2004 | White et al. | |
| 6,851,615 B2 | 2/2005 | Jones | |
| 6,915,170 B2 | 7/2005 | Engleson et al. | |
| 6,960,192 B1 | 11/2005 | Flaherty et al. | |
| 6,993,402 B2 | 1/2006 | Klass et al. | |
| 7,017,623 B2 | 3/2006 | Tribble et al. | |
| 7,061,831 B2 | 6/2006 | De La Huerga | |
| 7,074,205 B1 | 7/2006 | Duffy et al. | |
| 7,074,209 B2 | 7/2006 | Evans et al. | |
| 7,096,072 B2 | 8/2006 | Engleson et al. | |
| 7,103,419 B2 | 9/2006 | Engleson et al. | |
| 7,107,106 B2 | 9/2006 | Engleson et al. | |
| 7,115,113 B2 | 10/2006 | Evans et al. | |
| 7,117,041 B2 | 10/2006 | Engleson et al. | |
| 7,161,488 B2 | 1/2007 | Frasch | |
| 7,171,277 B2 | 1/2007 | Engleson et al. | |
| 7,236,936 B2 | 6/2007 | White et al. | |
| 7,364,067 B2 | 4/2008 | Steusloff et al. | |
| 7,370,797 B1 | 5/2008 | Sullivan et al. | |
| 7,384,410 B2 | 6/2008 | Eggers et al. | |
| 7,470,266 B2 | 12/2008 | Massengale et al. | |
| 7,483,756 B2 | 1/2009 | Engleson et al. | |
| 7,722,083 B2 | 5/2010 | McCarthy et al. | |
| 7,727,196 B2 | 6/2010 | Neer | |
| 7,771,385 B2 | 8/2010 | Eggers et al. | |
| 7,813,939 B2 | 10/2010 | Clements et al. | |
| 7,834,816 B2 | 11/2010 | Marino et al. | |
| 7,922,073 B2 | 4/2011 | de la Huerga | |
| 7,933,780 B2 | 4/2011 | De La Huerga | |
| 7,976,508 B2 | 7/2011 | Hoag | |
| 7,991,627 B2 | 8/2011 | Hutchinson et al. | |
| 8,035,517 B2 | 10/2011 | Gibson | |
| 8,133,178 B2 | 3/2012 | Brauker et al. | |
| 8,151,835 B2 | 4/2012 | Khan et al. | |
| 8,240,550 B2 | 8/2012 | Steusloff et al. | |
| 8,303,547 B2 | 11/2012 | Brown | |
| 8,328,082 B1 | 12/2012 | Bochenko et al. | |
| 8,480,834 B2 | 7/2013 | Rice et al. | |
| 8,505,809 B2 | 8/2013 | Steusloff et al. | |
| 8,636,202 B2 | 1/2014 | Keefe et al. | |
| 8,639,521 B2 | 1/2014 | Eggers et al. | |
| 8,639,525 B2 | 1/2014 | Levine et al. | |
| 8,645,154 B2 | 2/2014 | Eggers et al. | |
| 2001/0056258 A1 | 12/2001 | Evans | |
| 2002/0040208 A1 | 4/2002 | Flaherty et al. | |
| 2002/0077852 A1 | 6/2002 | Ford et al. | |
| 2002/0088131 A1 | 7/2002 | Baxa et al. | |
| 2002/0098598 A1 | 7/2002 | Coffen et al. | |
| 2002/0099334 A1 | 7/2002 | Hanson et al. | |
| 2002/0177811 A1 | 11/2002 | Reilly et al. | |
| 2002/0188259 A1 | 12/2002 | Hickle et al. | |
| 2003/0012701 A1 | 1/2003 | Sangha et al. | |
| 2003/0052787 A1 | 3/2003 | Zerhusen et al. | |
| 2003/0055685 A1 | 3/2003 | Cobb et al. | |
| 2003/0065537 A1 | 4/2003 | Evans | |
| 2003/0088238 A1 | 5/2003 | Poulsen et al. | |
| 2003/0135388 A1 | 7/2003 | Martucci et al. | |
| 2003/0139701 A1 | 7/2003 | White et al. | |
| 2003/0139706 A1 | 7/2003 | Gray | |
| 2003/0140929 A1 | 7/2003 | Wilkes et al. | |
| 2003/0174326 A1 | 9/2003 | Rzasa et al. | |
| 2004/0051368 A1 | 3/2004 | Caputo et al. | |
| 2004/0082918 A1 | 4/2004 | Evans et al. | |
| 2004/0092885 A1 | 5/2004 | Duchon et al. | |
| 2004/0103951 A1 | 6/2004 | Osborne et al. | |
| 2004/0104271 A1 | 6/2004 | Martucci et al. | |
| 2004/0186437 A1 | 9/2004 | Frenette et al. | |
| 2004/0204673 A1 | 10/2004 | Flaherty | |
| 2005/0055242 A1 | 3/2005 | Bello et al. | |
| 2005/0101905 A1 | 5/2005 | Merry | |
| 2005/0106225 A1 | 5/2005 | Massengale et al. | |
| 2005/0107923 A1 | 5/2005 | Vanderveen | |
| 2005/0165559 A1 | 7/2005 | Nelson | |
| 2005/0182358 A1 | 8/2005 | Veit et al. | |
| 2005/0277890 A1 | 12/2005 | Stewart et al. | |
| 2006/0079767 A1 | 4/2006 | Gibbs et al. | |
| 2006/0079843 A1 | 4/2006 | Brooks et al. | |
| 2006/0116639 A1 | 6/2006 | Russell | |
| 2006/0122577 A1 | 6/2006 | Poulsen et al. | |
| 2006/0144942 A1 | 7/2006 | Evans et al. | |
| 2006/0190302 A1 | 8/2006 | Eggers et al. | |
| 2006/0226089 A1 | 10/2006 | Robinson et al. | |
| 2006/0229551 A1 | 10/2006 | Martinez et al. | |
| 2006/0253346 A1 | 11/2006 | Gomez | |
| 2006/0258985 A1 | 11/2006 | Russell | |
| 2006/0265186 A1 | 11/2006 | Holland et al. | |
| 2006/0287887 A1 | 12/2006 | Hutchinson et al. | |
| 2007/0043335 A1 | 2/2007 | Olsen et al. | |
| 2007/0135765 A1 | 6/2007 | Miller et al. | |
| 2007/0136218 A1 | 6/2007 | Bauer et al. | |
| 2007/0166198 A1 | 7/2007 | Sangha et al. | |
| 2007/0167919 A1 | 7/2007 | Nemoto et al. | |
| 2007/0186923 A1 | 8/2007 | Poutiatine et al. | |
| 2007/0191787 A1 | 8/2007 | Lim et al. | |
| 2007/0279625 A1 | 12/2007 | Rzasa et al. | |
| 2007/0299421 A1 | 12/2007 | Gibson | |
| 2008/0045930 A1 | 2/2008 | Makin et al. | |
| 2008/0051937 A1 | 2/2008 | Khan et al. | |
| 2008/0061153 A1 | 3/2008 | Hickle et al. | |
| 2008/0125724 A1 | 5/2008 | Monroe | |
| 2008/0191013 A1 | 8/2008 | Liberatore | |
| 2008/0208042 A1 | 8/2008 | Ortenzi et al. | |
| 2008/0234630 A1 | 9/2008 | Iddan et al. | |
| 2008/0243088 A1 | 10/2008 | Evans | |
| 2008/0294108 A1 | 11/2008 | Briones et al. | |
| 2008/0306439 A1 * | 12/2008 | Nelson et al. | 604/84 |
| 2009/0018494 A1 | 1/2009 | Nemoto et al. | |
| 2009/0030730 A1 | 1/2009 | Dullemen et al. | |
| 2009/0036846 A1 | 2/2009 | Dacquay et al. | |
| 2009/0043253 A1 | 2/2009 | Podaima | |
| 2009/0069714 A1 | 3/2009 | Eichmann et al. | |
| 2009/0085768 A1 | 4/2009 | Patel et al. | |
| 2009/0126483 A1 | 5/2009 | Blendinger et al. | |

(56) References Cited

U.S. PATENT DOCUMENTS

| | | |
|---|---|---|
| 2009/0149744 A1 | 6/2009 | Nemoto et al. |
| 2009/0157008 A1 | 6/2009 | Vitral |
| 2009/0159654 A1 | 6/2009 | Grimard |
| 2009/0294521 A1 | 12/2009 | de la Huerga |
| 2010/0065643 A1 | 3/2010 | Leyvraz et al. |
| 2010/0152562 A1 | 6/2010 | Goodnow et al. |
| 2010/0153136 A1 | 6/2010 | Whittacre et al. |
| 2010/0174266 A1 | 7/2010 | Estes |
| 2010/0179417 A1 | 7/2010 | Russo |
| 2010/0262002 A1 | 10/2010 | Martz |
| 2010/0280486 A1 | 11/2010 | Khair et al. |
| 2010/0305499 A1 | 12/2010 | Matsiev et al. |
| 2011/0060198 A1 | 3/2011 | Bennett et al. |
| 2011/0093279 A1 | 4/2011 | Levine et al. |
| 2011/0111794 A1 | 5/2011 | Bochenko et al. |
| 2011/0112473 A1 | 5/2011 | Bochenko et al. |
| 2011/0112474 A1 | 5/2011 | Bochenko et al. |
| 2011/0152824 A1 | 6/2011 | DiPerna et al. |
| 2011/0160655 A1 | 6/2011 | Hanson et al. |
| 2011/0176490 A1 | 7/2011 | Mehta et al. |
| 2011/0220713 A1 | 9/2011 | Cloninger |
| 2011/0224649 A1 | 9/2011 | Duane et al. |
| 2011/0264069 A1 | 10/2011 | Bochenko |
| 2011/0313349 A1 | 12/2011 | Krulevitch et al. |
| 2012/0004542 A1 | 1/2012 | Nemoto et al. |
| 2012/0037266 A1 | 2/2012 | Bochenko |
| 2012/0041355 A1 | 2/2012 | Edman et al. |
| 2012/0222468 A1 | 9/2012 | Nelson et al. |
| 2012/0226446 A1 | 9/2012 | Nelson et al. |
| 2012/0226447 A1 | 9/2012 | Nelson et al. |
| 2012/0325330 A1 | 12/2012 | Prince et al. |
| 2013/0018356 A1 | 1/2013 | Prince et al. |
| 2013/0105568 A1 | 5/2013 | Jablonski et al. |
| 2013/0135388 A1 | 5/2013 | Samoto et al. |
| 2013/0181046 A1 | 7/2013 | Fedorko et al. |
| 2013/0204227 A1 | 8/2013 | Bochenko et al. |
| 2013/0225945 A1 | 8/2013 | Prince et al. |
| 2013/0226137 A1 | 8/2013 | Brown |
| 2013/0327822 A1 | 12/2013 | Keefe et al. |
| 2014/0039383 A1 | 2/2014 | Dobbles et al. |
| 2014/0060729 A1 | 3/2014 | Srnka et al. |
| 2014/0142975 A1 | 5/2014 | Keefe et al. |

OTHER PUBLICATIONS

Google Scholar Search [Jul. 21, 2014].

\* cited by examiner

MEDICATION DOSE PREPARATION AND TRANSFER SYSTEM

RELATED APPLICATION

This application claims priority to U.S. Pat. App. Ser. No. 61/497,855 filed on Jun. 16, 2011, the contents of which are hereby fully incorporated by reference.

FIELD

The subject matter described herein relates to a medication dose preparation and transfer apparatus used for identifying medication within a medication container, measuring an amount of medication withdrawn from the medication container and transferred to a secondary container (e.g. syringe), tracking the amount of medication actually administered to a patient and tracking the amount of any residual medication disposed of as waste.

BACKGROUND

There are a number of patient clinical settings including in-hospital, outpatient and emergency medical services (EMS) that require transfer of medications from original pharmaceutical manufacturer's primary containers to secondary containers to facilitate caregiver administration to patients. When medications are transferred to secondary containers it is standard clinical best practice to label them to reduce the potential for medication errors. However, due to dose measurement mistakes, incorrect transfer of labeling information and other factors, errors continue to occur when caregivers transfer medications from primary containers (vials to syringes) or prepare partial doses (empty syringe withdraws of a partial amount from a primary vial).

SUMMARY

In one aspect, an apparatus for transferring medication from a primary medication container to a manually injectable secondary medication container is provided. The apparatus includes a fluid channel, a primary medication container coupling, a secondary medication coupling, at least one identification sensor and a communications module. The fluid channel terminates at a primary medication container port on a first end and a secondary medication container port on a second end. The primary medication container coupling is configured to fluidically couple the primary medication container to the primary medication container port. The secondary medication container coupling is configured to fluidically couple the secondary medication container to the secondary medication container port. The at least one identification sensor senses (i) an information transfer element on the primary medication container and (ii) an information transfer element on the secondary medication container with the information transfer element on the primary container being used to characterize the medication. The communications module transmits data obtained by and/or derived from the at least one identification sensor to a remote computing system to associate the medication in the primary medication container as having been transferred to the secondary medication container.

The primary medication container coupling can include a spike to penetrate a barrier of the primary medication container. The secondary medication container coupling can include a female luer fitting to mate with a male luer fitting of the secondary medication container. The primary medication container can be vial with a vial adapter having the information transfer element disposed thereon.

The secondary medication container can be a syringe with the information transfer element disposed upon an encoded hub attached to a fluid outlet of the syringe (which in turn is configured to fluidically couple with the secondary medication container port). The communications module can wirelessly transmit data to and/or receive data from the remote computing system.

A first identification sensor can sense the information transfer element of a primary medication container and a second identification sensor can sense the information transfer element of the secondary medication container. The information transfer element on at least one of the primary medication container and the secondary medication container can include or be a unique identifier such as a serial number.

The at least one flow sensor can characterize an amount of medication passing through the fluid channel such that the communications module transmits data indicating same. In some implementations, the at least one flow sensor can be a bi-directional flow sensor measuring fluid flow in two opposing directions and the data transmitted can separately characterize fluid flow in both opposing directions.

Memory can be included that stores data such as data obtained from the at least one identification sensor and/or the at least one flow sensor. At least one data processor (e.g., a CPU/microprocessor, etc.) can process data stored in the memory.

A user indicator (e.g., an interface, display, etc.) can be provided that provides visual and/or audio feedback to a user. The indicator can be interactive allowing the user to change one or more operating parameters (e.g., alarm override, enter patient information and the like). The user indicator can display a wide range of information, including but not limited to: medication name, medication category, recommended dosage, secondary medication container fill volume, medication waste volume, secondary medication container identifier, and partial dosage volume.

In some implementations, the entire apparatus can be disposable. In other implementations, only a portion of the apparatus is disposable (with the remaining portion being reusable). With this latter arrangement, the fluid channel can be selectively removable to avoid medication cross-contamination and/or sterility issues. With a removable fluid channel, there can be memory within or otherwise coupled to the removable fluid channel. Such memory can have and/or store a unique identifier (e.g., serial number, etc.).

The remote computing system can be, for example, one or more of medication management devices and systems, electronic medical records systems, pharmacy management and fulfillment systems, medication storage systems, medication dispensing stations, and medication waste disposal systems.

The fluid channel can undertake a variety of geometries. It can be linear, at least partially curved, and angled. With the latter, the fluid channel can have at least one 90 degree angle, and in one implementation, it can have at least two 90 degree angles.

The fluid channel can terminate at a patient outlet which can, for example, lead to an IV line for a patient. The fluid channel can include a first sub-channel connecting the primary medication container port with the patient outlet and a second sub-channel extending at an angle from the first sub-channel terminating on one end at the first sub-channel and on a second end at the secondary medication container port. A bi-directional flow sensor can measure the flow of medication in both directions within the second sub-channel as it is transferred to the secondary medication container and as it is expelled from the secondary medication container. With such an arrangement, the communications module can transmit data characterizing the medication flow detected by the bi-direction sensor.

At least one check valve can be incorporated to prevent the medication expelled from the secondary medication container from flowing towards the primary medication container port and/or to prevent medication extracted from the primary medication container from flowing back towards the primary medication container port. Removable channel caps can be employed that are secured to the primary medication container port and the secondary medication container port.

A housing can be provided through which the fluid channel traverses. Such housing can have a size and shape to allow a user to hold the housing and a primary medication container in a first hand and to operate the manually injectable secondary medication container using a second hand.

The fluid channel can include a primary fluid channel terminating at two sub-channels. The two sub-channels can be at an angle in relation to the primary fluid channel and being parallel in relation to each other, the sub-channels respectively terminating in the primary medication container port and the secondary medication container port.

A display can be displayed on a housing (i.e., an outer surface of a housing) that envelopes the fluid channel. The communications module can receive data from at least one computing system characterizing the medication, at least a portion of the received data being displayed on the display. It will be appreciated that the communications module can transmit data to a first computing system while receiving data from a second computing system. At least a portion of the information being displayed can include one or more of: information about the fluid transfer process, user guidance, information about the dose to be administered, information about the dose administered to a patient, and patient specific medication administration guidelines or restrictions. The received data can include one or more of: medication delivery order data, patient-specific identifiers, general or medication-specific dosing limits, data for contraindication checking, Broselow color/classification, patient drug allergies, patient weight, medication data, patient specific data, procedural cautionary data, error prevention data, dose time data, physician instructions, drug manufacturer instructions, precautions associated with the medication, and contraindications associated with the medication.

The at least one identification sensor can detect the information transfer element using one or more technologies such as optical, magnetic, mechanical, conductive, capacitive, inductive, proximity sensors, infrared, and switchable RFID.

In an interrelated aspect, an apparatus for transferring medication from a primary medication container to a manually injectable secondary medication container includes a fluid channel, a primary medication container, a secondary medication container, at least one fluid flow sensor, and a communications module. The fluid channel terminates at a primary medication container port on a first end and a secondary medication container port on a second end. The primary medication container coupling is configured to fluidically couple the primary medication container to the primary medication container port. The secondary medication container coupling is configured to fluidically couple the secondary medication container to the secondary medication container port. The at least one flow sensor to sense medications flowing through the fluid channel. The communications module transmits data obtained by and/or derived from the at least one flow sensor to a remote computing system and, in some implementations, receives data from one or more remote computing systems associated with the medication and/or the patient.

Systems can be provided that additionally include a dose preparation and transfer apparatus and one or more of a primary medication container and manually injectable secondary medication container. Kits can be provided that include dose preparation and transfer apparatus as well as one or more of a primary medication container and a manually injectable container.

In a further interrelated aspect, a dose preparation and transfer apparatus detects a medication identification code (information transfer element) on a primary medication container, detects an identifier (information transfer element) of a secondary medication container, and transmits data to a remote computing system that characterizes the detected medication identification code and the detected identifier. In some implementations, the dose preparation and transfer apparatus further detects an amount of medication transferred from the primary container to the secondary container and data characterizing same is transmitted to the remote computing system.

Apparatus, systems, methods and articles are described to prepare and track medication containers as they are prepared, administered to patients and, in some cases, disposed of. Information such as medication type, concentration, and volume are associated with medication containers during preparation and this information can later be consumed/utilized when administering the medication from a container to a patient. Disposing of any remaining medication can also be tracked (which can be advantageous in connection with controlled substances). In some examples, medication is transferred from a container such as a vial into a syringe and data characterizing the medication is associated with the syringe (e.g., a bar code, a record in a look-up table, etc.). The medication in this syringe can then be injected into a patient via, for example, a medication injection site which can automatically identify the medication container and/or its contents. Any remaining contents of this syringe can be injected into a waste disposal system which can also automatically identify the medication container and/or its contents (and log the container and amount of disposed medication disposed).

DESCRIPTION OF THE DRAWINGS

The accompanying drawings, which are incorporated in and constitute a part of this specification, show certain aspects of the subject matter disclosed herein and, together with the description, help explain some of the principles associated with the disclosed embodiments. In the drawings.

Like reference symbols in the various drawings indicate like or similar elements.

DETAILED DESCRIPTION

Figure 1:
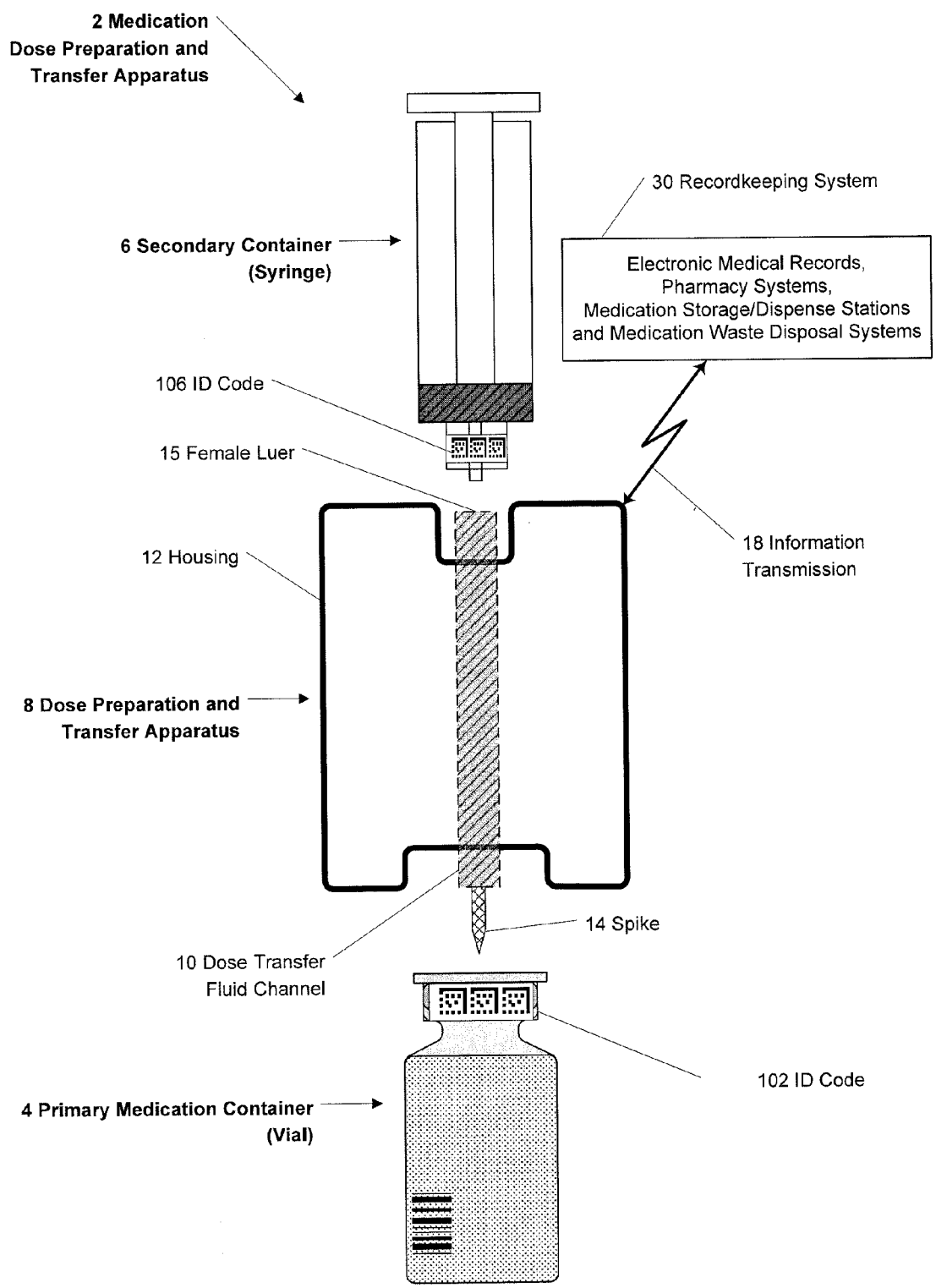
FIG. 1 is a diagram illustrating a medication dose preparation and transfer system.

FIG. 1 is a diagram illustrating a medication dose preparation and transfer system 2. System 2 comprises primary medication container 4, secondary medication container 6, dose preparation and transfer apparatus 8 and interconnecting dose transfer fluid channel 10. Fluid channel 10 can include spike 14 for connection to primary medication container 4 and female luer fitting 15 for connection to secondary container 6. Following attachment of container 4 and container 6, fluid from container 4 can be transferred to container 6 through dose transfer channel 10. Information 18 about containers 4 and 6 and the medication transferred through fluid channel 10 can be transmitted (via, for example, a communications module) to recordkeeping system 30 (which may be coupled wirelessly, via a hard-wired communications network, or a combination of both). Recordkeeping system 30 (including healthcare information computing systems) can include one or more of: medication management devices and systems, electronic patient medical records, medication administration records, pharmacy records, medication storage station inventory records, records accounting for the disposal of medication wastes, and the like.

A healthcare provider can select vial 4 from an array of available vials and transfer the medication and medication information to a patient's medication injection site for administration. Examples of medication injection sites and related data collection systems are described in U.S. patent application Ser. Nos. 12/614,276, 12/765,707 and 12/938,300 all entitled "Medication Injection Site and Data Collection System," the contents of which are hereby fully incorporated by reference.

Medication container 4 and secondary container 6 can be joined by a dose preparation and transfer apparatus 8 to form medication dose preparation and transfer system 2. Housing 12 can contain hardware, software and mechanical elements for characterizing the transferred medication (e.g., identify and measure amount of transferred medication, determine transfer time, etc.). A dose transfer fluid channel 10 can connect each container (4 and 6) forming a transfer pathway. Fluid channel 10 can be integrated within housing 12 or be separate. When separate, housing 12 is reusable and can be used with many fluid channels 10 that can be made sterile and disposable for single patient use. Disposable flow channel 10 can be sterilized and be part of a kit including a sterile pouch enveloping the disposable sub-housing. Housing 12 and/or fluid channel 10 can be assigned serial numbers for identification which can be read by or received from recordkeeping system 30. One end of fluid channel 10 can have spike 14 to puncture medication container 4 to access the medication for transfer to secondary container (e.g. syringe) 6. The other end of fluid channel 10 can be a female luer type fitting 15 to accept a male luer fitting on secondary container 6.

The dose preparation and transfer apparatus 8 allows a desired amount of medication in vial 4 to be transferred to a syringe 6 through fluid channel 10. Syringe 6 can initially be provided empty, or in the case of a medication mixture or dilution, can contain an existing volume of fluid. Syringe 6 can be attached to the medication dose preparation and transfer device to withdraw the medication from vial 4. Primary medication container 4's contents can be identified using an information transfer element ID Code 102 (medication name, manufacturer name, drug concentration, NDC code, volume contained, serial number, and other drug or patient specific information) on or associated with primary medication container 4. Secondary medication container 6 can be identified using an information transfer element (ID Code 106). These ID Codes will be described below.

Figure 2:
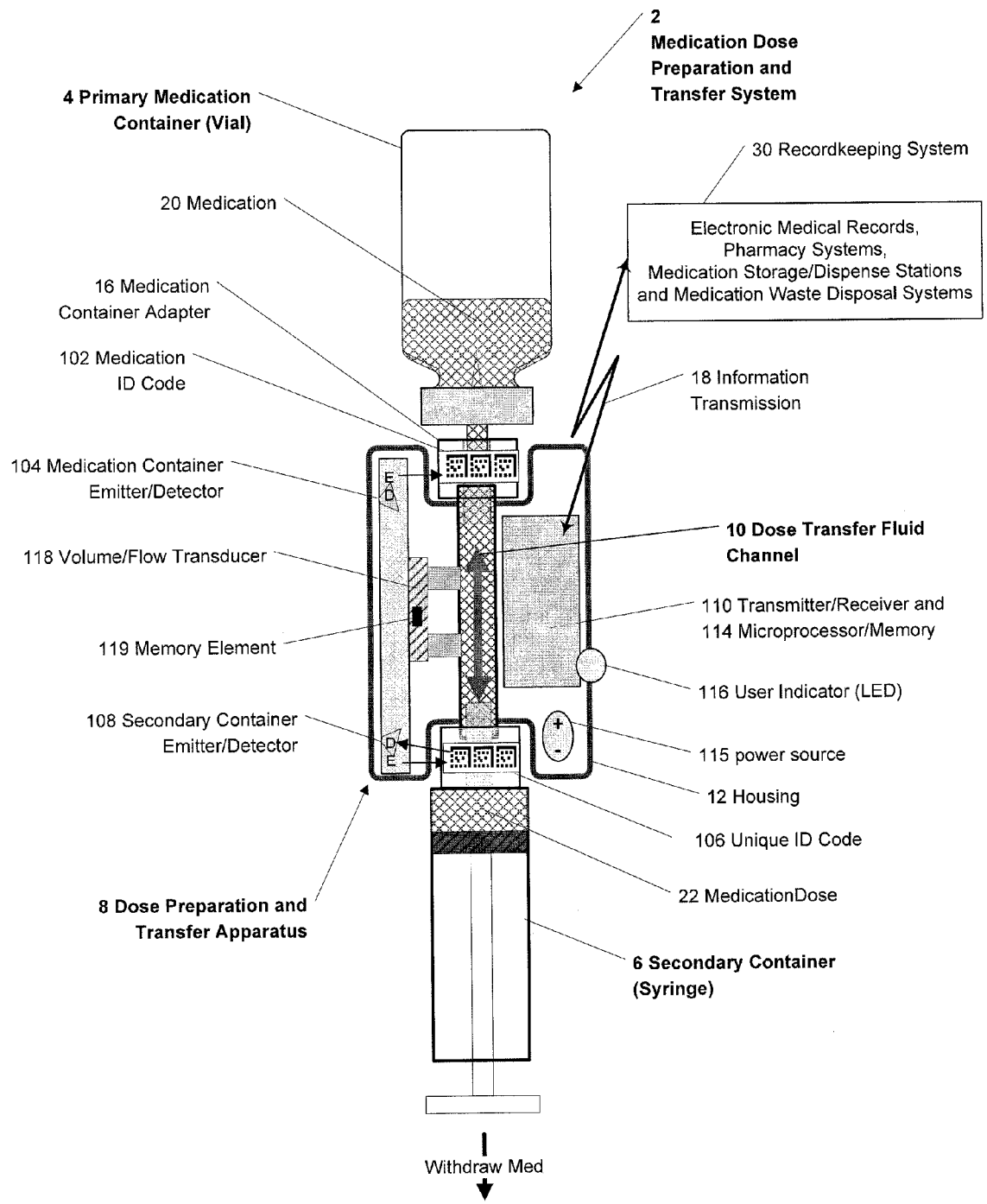
FIG. 2 is a diagram describing a detailed view of a medication dose preparation and transfer system as in FIG. 1.

FIG. 2 is a diagram describing a detailed view of a medication dose preparation and transfer system 2 as in FIG. 1. At the top of the figure, primary medication container (vial) 4 contains medication 20. At the bottom of vial 4 the open end can be closed by rubber closure and protected by flip off cap. Vial 4 can carry an information source (e.g., medication ID code 102) that provides detectable information indicative of the medication in primary container 4 and/or of the volume of the contents. Primary medication container (Vial) 4 as used herein refers to both vials and other medication containers such as pre-filled syringes and/or bags (except when explicitly disclaimed). It can be appreciated that many configurations of vial 4 can be manufactured and can function in system 2.

At the bottom of the figure, secondary container 6 can be a syringe with a syringe body, male luer fitting tip, plunger and plunger rod. It can be appreciated that many configurations of secondary container 12 can be manufactured and can function in system 2.

FIG. 2 further illustrates a medication dose preparation and transfer system 2 that comprises medication container adapter (vial adapter) 16 joined with information transfer element (ID Code 102). Vial adapter 16 can be a sterilizable plastic material and can comprise vial spike, spike cover, vial clips, a flow channel and a female luer fitting. It can be appreciated that many configurations of vial adapter 16 can be manufactured and can function in system 2 (provided that the vial adapter can create a sterile fluid pathway between the vial contents and the dose transfer fluid channel 10). Examples of vial adapter devices are described in U.S. patent application Ser. No. 13/282,255 entitled "Medication and Identification Information Transfer Apparatus", the contents of which is hereby fully incorporated by reference.

The vial adapter 16 can be a sterilizable injection molded plastic material consisting of element body, fluid inlet, fluid outlet, flow channel and ID Code 102.

ID Code 102 can be one or more of an optical source, a magnetic source, a mechanical source, a switchable RFID source, a conductive source, and/or a proximity source. One implementation can provide information encoded within the information element in the form of an optically detectable surface, reflective or absorbing light surface, and can be embedded into or on top of element body.

Alternatively, information provided by ID Code 102 can be a magnetically detectable strip similar to a credit card magnetic strip, facilitating a magnetic scan similar to credit card swiping, that is embedded into or on top of the information element body.

Further and alternatively, information provided by the information element can be a mechanically detectable feature consisting of Braille like features of bumps or ridges or valleys on the surface of or at the end of element body, facilitating mechanical detection by a micro switch or similar physical detection method.

Further and alternatively, information provided by information element can be an RFID tag located on the surface of element body, facilitating detection by an RFID reader. The antenna of the RFID tag can be switchable and can be OPEN prior to connection to the medication dose preparation and transfer apparatus 8. Upon connection to the dose preparation and transfer apparatus 8, the antenna can become CLOSED (or connected) facilitating RFID reader detection. When the container is disconnected from the dose preparation and transfer apparatus, the RFID tag antenna can again become OPEN.

Further and alternatively, information provided by information transfer element ID Code 102 can be in the form of a capacitive or inductive proximity feature on the surface of or embedded into element body, facilitating capacitive or inductive proximity detection.

The information element can be an integrated feature of the information transfer element such as etched or molded features. The information element can alternatively be adhered or deposited to the element body (i.e., information element can be a label, etc.) or embedded therein. In addition, the information element can be a separate element that extends around fluid outlet 54.

The encapsulated data within ID Code 102 can be formatted using an industry standard representation of the medication being characterized or a proprietary representation of the medication being characterized. The data can include one or more of: an NDC code (National Drug Code), a segment of the NDC code identifying the drug product, a segment of the NDC code identifying the drug package, a unique identifier code, a human readable alphanumeric, a machine readable code, a name of the medication, a manufacturer of the medication, a re-packager of the medication, a distributor of the medication, a strength of the medication, a dosage form of the medication, dose instructions for the medication, administration instructions for a specific patient, medication formulation, medication package form, medication package size, medication contained volume, medication package serial number, medication lot number, and medication expiration date. The encapsulated data can additionally or alternatively also include such information.

The ID Code 102 can be applied by any number of operations or steps in the medication supply chain prior to medication administration to a patient including, but not limited to: the original medication manufacturer, a pharmaceutical re-packager, a hospital pharmacy, a compounding pharmacy service, a healthcare professional or caregiver, a patient.

Secondary container 6 can be encoded with ID Code 106 to identify the container. ID Code 106 can be a unique number, code, symbol, serial number, random number, or other information describing a specific unique secondary container 6. A medication dose can be transferred from primary container 4 through fluid channel 10 into secondary container 6 by pulling on the plunger rod of syringe 6 and drawing medication dose 22 into it.

The ID Code 106 can be applied by any number of operations or steps in the supply chain of secondary container 6 prior to medication transfer including, but not limited to: the original secondary container manufacturer, a pharmaceutical re-packager, a compounding pharmacy service, a hospital pharmacy, a healthcare professional or caregiver, a patient. ID Code 106 can be one or more of an optical source, a magnetic source, a mechanical source, a switchable RFID source, a conductive source, and/or a proximity source. One implementation can provide information encoded within the information element in the form of an optically detectable surface, reflective or absorbing light surface, and can be embedded into or on top of the element body.

Alternatively, information provided by ID Code 106 can be a magnetically detectable strip similar to a credit card magnetic strip, facilitating a magnetic scan similar to credit card swiping, that is embedded into or on top of the information element body.

Further and alternatively, information provided by the information element can be a mechanically detectable feature consisting of Braille like features of bumps or ridges or valleys on the surface of or at the end of element body, facilitating mechanical detection by a micro switch or similar physical detection method.

Further and alternatively, information provided by ID Code 106's information element can be an RFID tag located on the surface of element body, facilitating detection by an RFID reader. The antenna of the RFID tag can be switchable and would be OPEN prior to connection to the medication dose preparation and transfer apparatus 8. Upon connection to the medication dose preparation and transfer apparatus 8, the antenna can become CLOSED (or connected) facilitating RFID reader detection. When the container is disconnected from the dose preparation and transfer apparatus, the RFID tag antenna can again become OPEN.

Further and alternatively, information provided by ID Code 106's information element can be in the form of a capacitive or inductive proximity feature on the surface of or embedded into element body, facilitating capacitive or inductive proximity detection.

ID Code 106's information element can be an integrated feature of the information transfer element such as etched or molded features. The information element can alternatively be adhered or deposited to the element body (i.e., information element can be a label, etc.) or embedded therein. In addition, the information element can be a separate element that extends around fluid outlet. Further, ID Code 106 can be part of an extension or a similar vial adapter adapter 16 that can attach to the fluid outlet of secondary container 6 in a way that once connected becomes permanently or semi-permanently affixed.

Dose preparation and transfer apparatus 8 can have housing 12 that encloses a power source 115, hardware and software elements 110 and 114. Within apparatus 8 are dose transfer fluid channel 10 (either built-in or separately clipped-in), medication container emitter/detector 104 to detect and transfer ID Code 102 to microprocessor/memory 114, secondary container emitter/detector 108 to detect and transfer ID Code 106 to microprocessor/memory 114 (e.g., a data processor, etc.), volume/flow transducer 118 to monitor and measure fluid transfer, a user indicator 116 can be provided to indicate various steps in the process and provide feedback to the user. Other user indicators can include a display which will be discussed later.

When dose transfer fluid channel 10 is separate from dose preparation transfer apparatus 8, fluid channel 10 can be clipped-in in any number of ways to facilitate mating with apparatus 8 for the connection of volume/flow transducer 118 to monitor and measure fluid transfer including, but not limited to: snap fit of fluid channel 10 into a cavity within housing 12, snap fit of fluid channel 10 onto the outside of housing 12, an electrical connector, an inductive connector, an optical connection, etc.

Alternately, the separate fluid channel 10 can include volume/flow transducer 118 and/or a memory element 119. The memory element 119 can include any one of calibration data, serial number or other unique information.

Dose preparation transfer apparatus 8 can also contain a communications module (sometimes referred to as a wireless radio) 110 for transmission of information 18 to a remote recordkeeping system 30. Recordkeeping system 30 will be discussed later and can be a remote computing system. Information 18 can be bi-directional and can include transfer of data from recordkeeping system 30 (including a medication management system or a healthcare information system) to dose preparation and transfer apparatus 8. Information that can be transferred from record keeping system 30 to dose transfer apparatus 8 includes but is not limited to medication delivery order data, patient-specific identifiers, general or medication-specific dosing limits, data for contraindication checking, Broselow color/classification, patient drug allergies, patient weight, or other information relevant for ensuring the medication being transferred is the right medication and that the resultant dose transferred to secondary container 6 is correct for the intended patient use.

Figure 3:
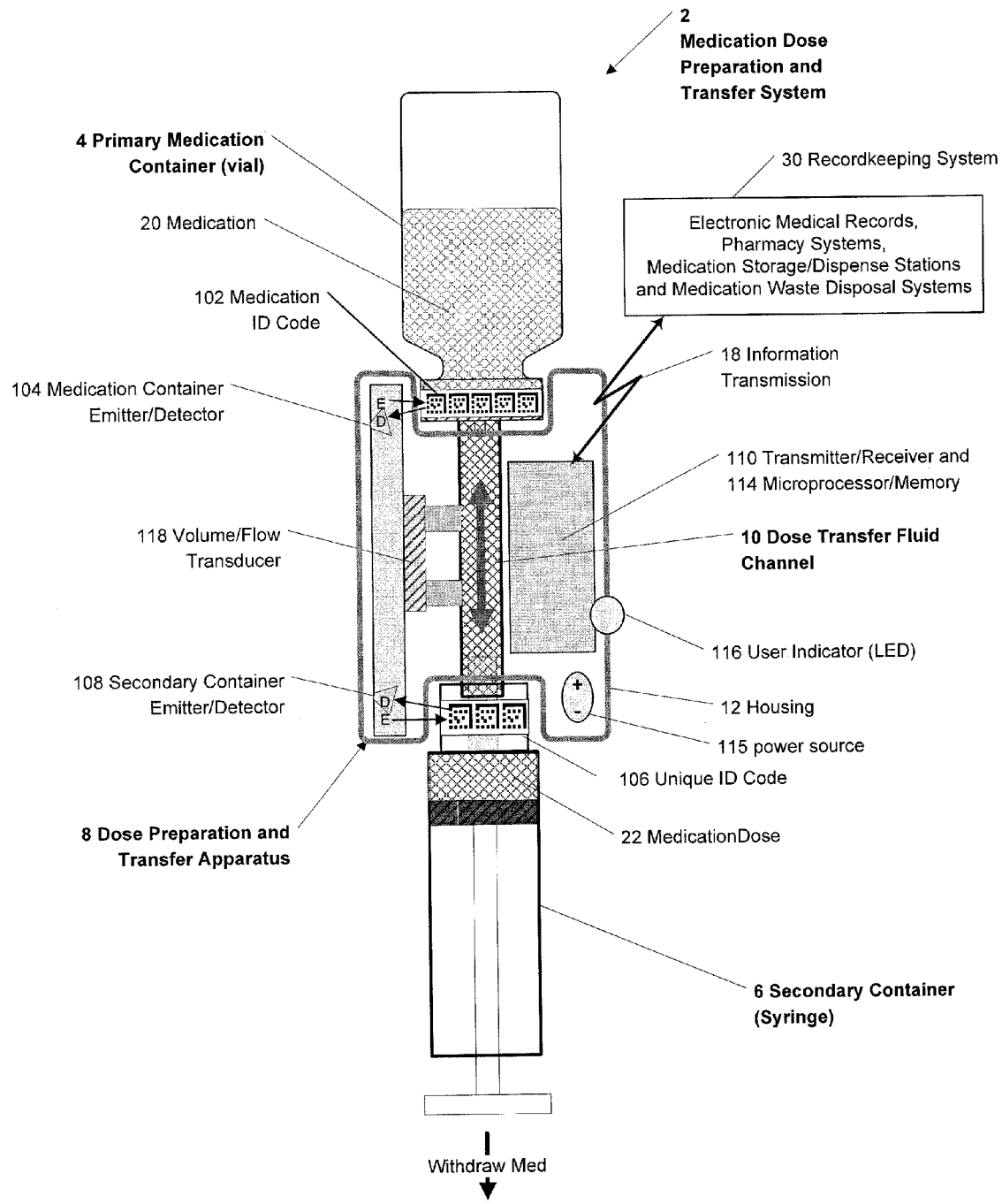
FIG. 3 is a diagram describing a detailed view of a second medication dose preparation and transfer system as in FIG. 1.

FIG. 3 is a diagram describing a detailed view of a second medication dose preparation and transfer system as in FIG. 1. In this variation, medication ID Code 102 can be placed on the closure rim of the primary medication container 4. No vial adapter 16 is needed. Here, medication container emitter/detector 104 can directly identify medication ID Code 102 from primary medication container (vial) 4. The other features and functions of dose preparation and transfer apparatus 8 described in FIG. 2 can be the same.

Figure 4:
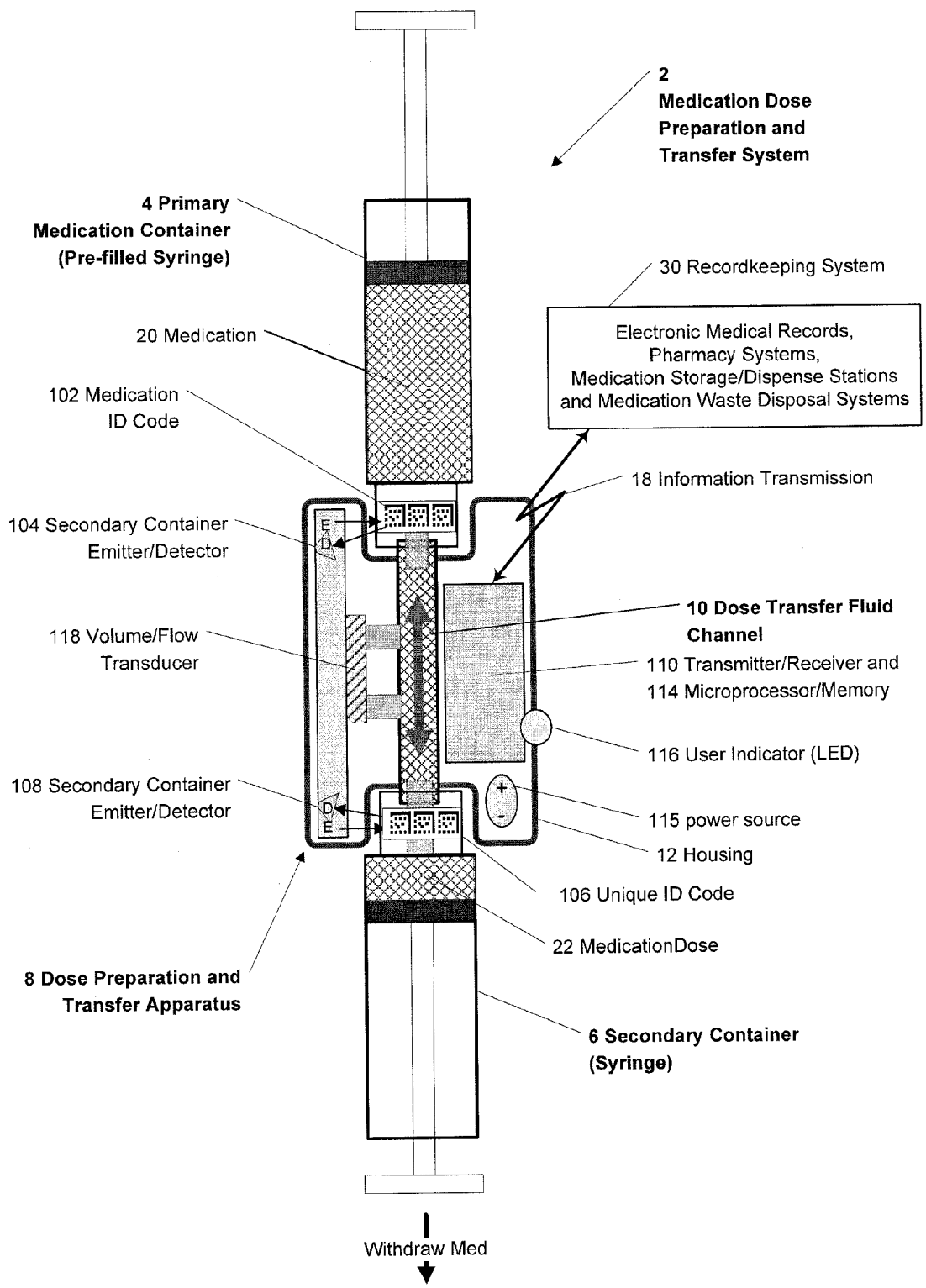
FIG. 4 is a diagram describing a detailed view of a third medication dose preparation and transfer system as in FIG. 1.

FIG. 4 is a diagram describing a detailed view of a third medication dose preparation and transfer system as in FIG. 1. In this variation, medication ID Code 102 is placed on the outlet of a prefilled syringe 4. Here, medication container emitter/detector 104 can directly identify medication ID Code 102 from primary medication container 4 (syringe). The other features and functions of dose preparation and transfer apparatus 8 described in FIG. 2 can be the same.

Figure 5:
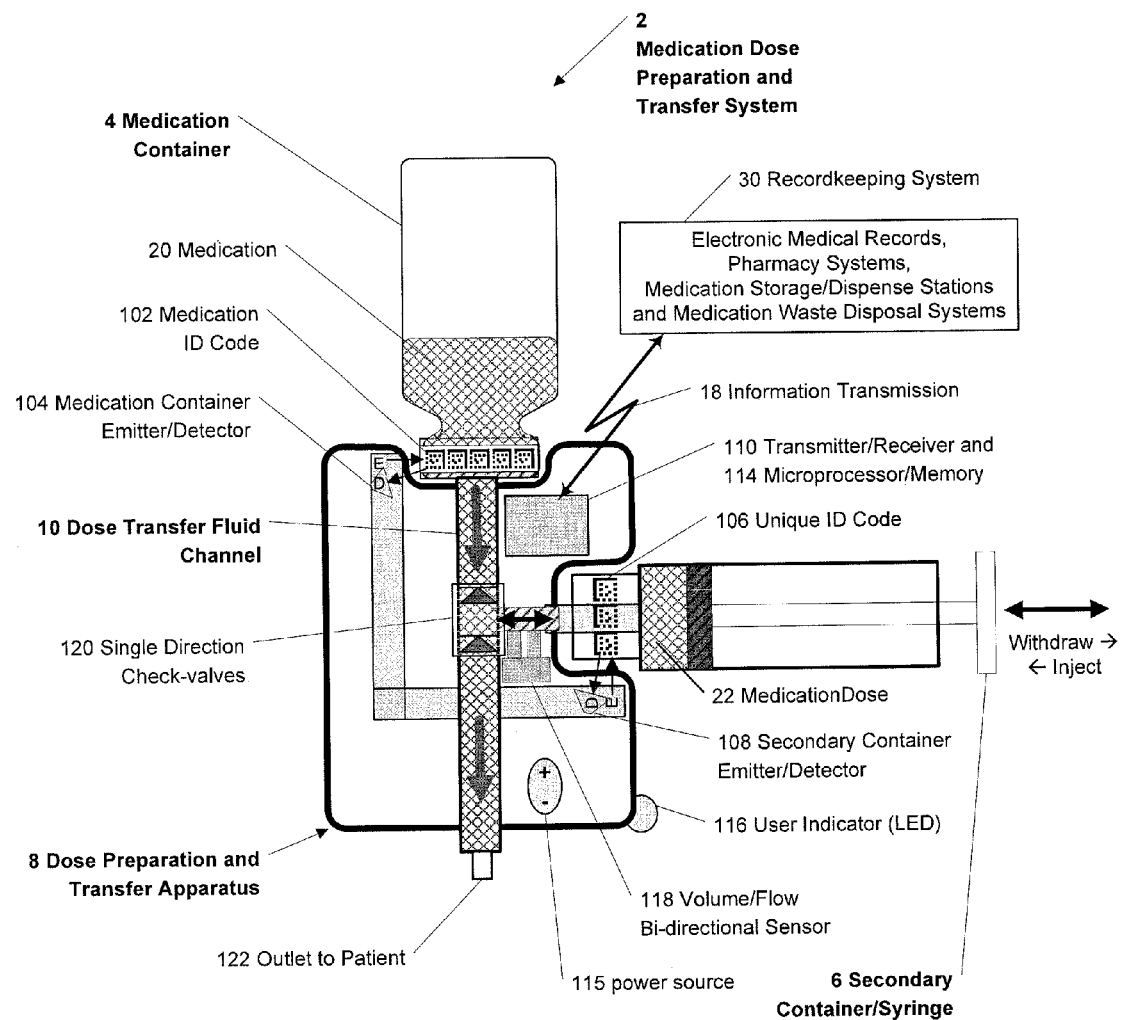
FIG. 5 is a diagram describing a detailed view of a fourth medication dose preparation and transfer system as in FIG. 1.

FIG. 5 is a diagram describing a detailed view of a fourth medication dose preparation and transfer system as in FIG. 1. In this implementation, medication ID Code 102 can be placed on the closure rim of primary medication container 4 and secondary container (syringe) 6 and located at right angle (or any angle convenient to facilitate use) to the fluid transfer channel 10. Here, medication container emitter/detector 104 can directly identify medication ID Code 102 from primary medication container 4 (vial). Secondary container emitter/detector 108 can identify ID Code 106. Additionally dose transfer fluid channel 10 can form a "T" (or other angled junction).

A single direction set of check valves 120 can be located at the junction to control flow through channel 10. When a plunger rod of the secondary container (syringe) 6 is pulled (withdrawn), fluid is removed from primary medication container 4 and passes into syringe 6. The upstream check valve allows flow to the secondary container 6 and the downstream check valve prevents backflow (or air) from the patient outlet 122. Here, a volume/flow bi-directional sensor 118 can measure fluid transfer into the secondary container 6 from vial 4. The secondary container 6 can be removed for administration to a patient as in FIG. 3. Alternately, the entire dose preparation and transfer apparatus 8 can be attached to a patient's administration injection port (not shown). In this variation, fluid outlet 122 is attached to the injection port and medication dose 22 is injected by pushing on the syringe plunger rod. Check valves 120 direct flow to the patient. The upstream check valve prevents flow back into primary container 4 and the downstream check valve allows fluid flow to the patient. The other features and functions of dose preparation and transfer apparatus 8 described in FIG. 2 are the same.

Figure 6:
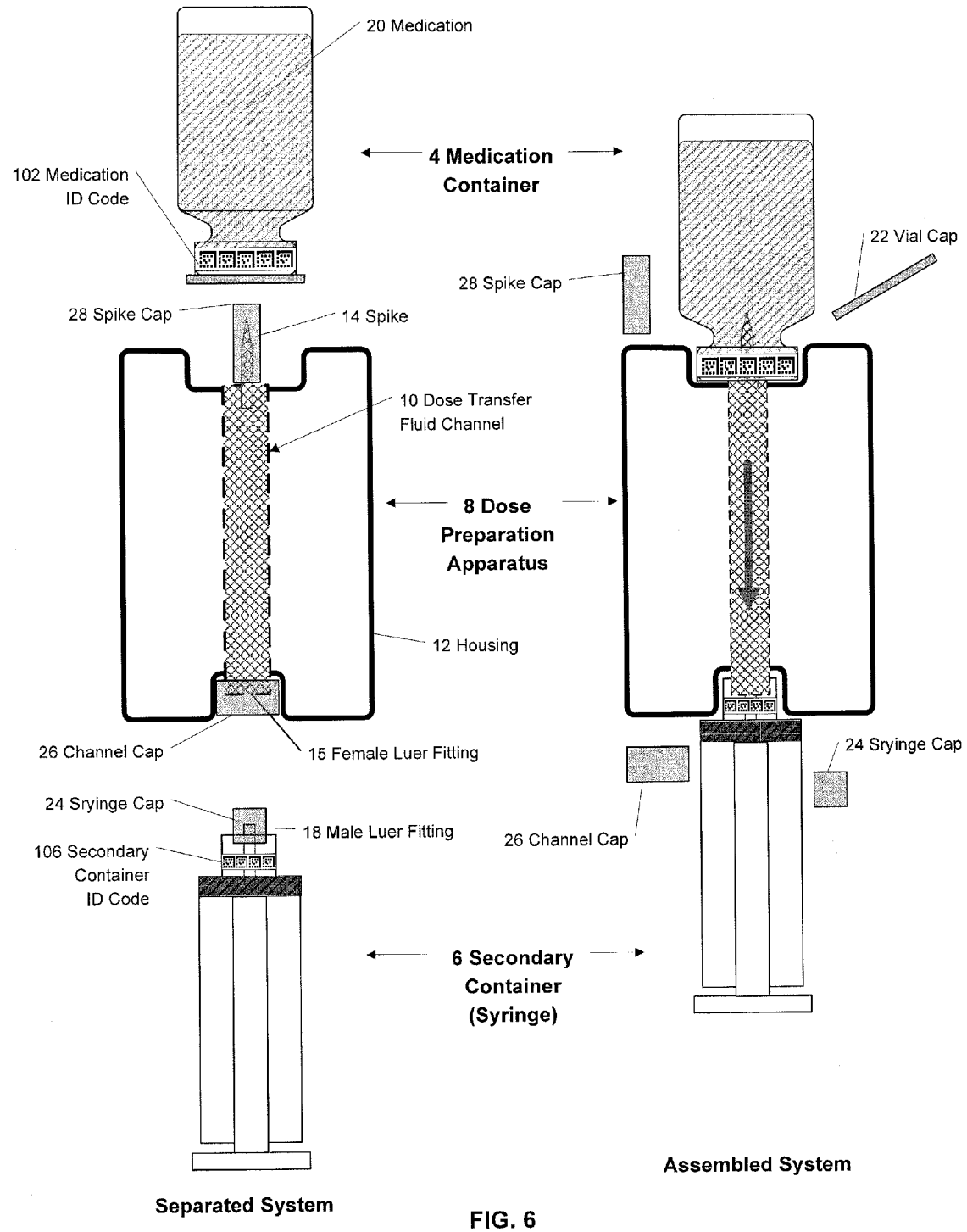
FIG. 6 is a diagram describing the assembly of a medication dose preparation and transfer apparatus with medication containers as in FIG. 3.

FIG. 6 is a diagram describing the assembly of a medication dose preparation and transfer apparatus with medication containers as in FIG. 1. Primary medication container 4 and secondary medication container 6 can be prepared for use by removing their respective protective caps 22 and 24. Dose fluid transfer channel 10 can be prepared by removing channel cap 26 and spike cap 28. These caps protect the containers and fluid transfer channel 10 when they are provided sterile (fluid path is sterile). Dose preparation apparatus 8 may be held in a first hand and medication container 4 (vial) is held in a second hand. Fluid channel 10's fluid inlet spike 14 can be inserted through a sterile closure stopper in the vial. Secondly, secondary container 6 can be attached to the fluid channel outlet female lure fitting 15 (this can be a slip luer or luer lock type fitting).

Figure 7:
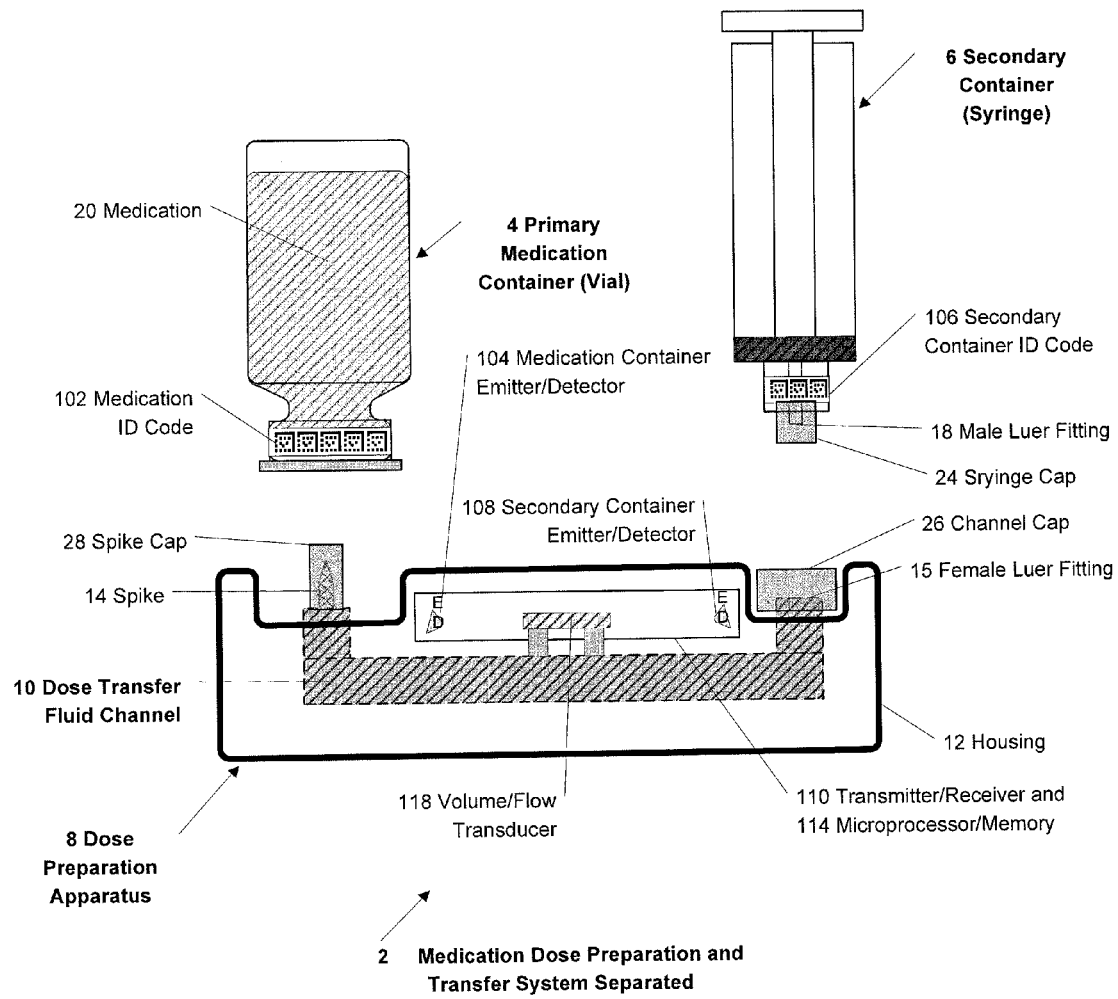
FIG. 7 is a diagram describing a detailed view of a fifth medication dose preparation and transfer system as in FIG. 1.

FIG. 7 is a diagram describing a detailed view of a fifth medication dose preparation and transfer system 2 as in FIG. 1. In this implementation dose transfer fluid channel 10 can be "U" shaped. This can provide for an alternate user configuration where both primary container 4 and secondary container 6 are on the same side of dose preparation apparatus 8. Medication ID Code 102 is placed on the closure rim of the primary medication container 4. Medication container emitter/detector 104 directly identifies medication ID Code 102 from primary medication container (vial) 4. Alternately, fluid transfer channel 10 can be "L" shaped, "J" shaped or otherwise shaped to facilitate use. The other features and functions of dose preparation and transfer apparatus 8 described in FIG. 2 can be the same.

Figure 8:
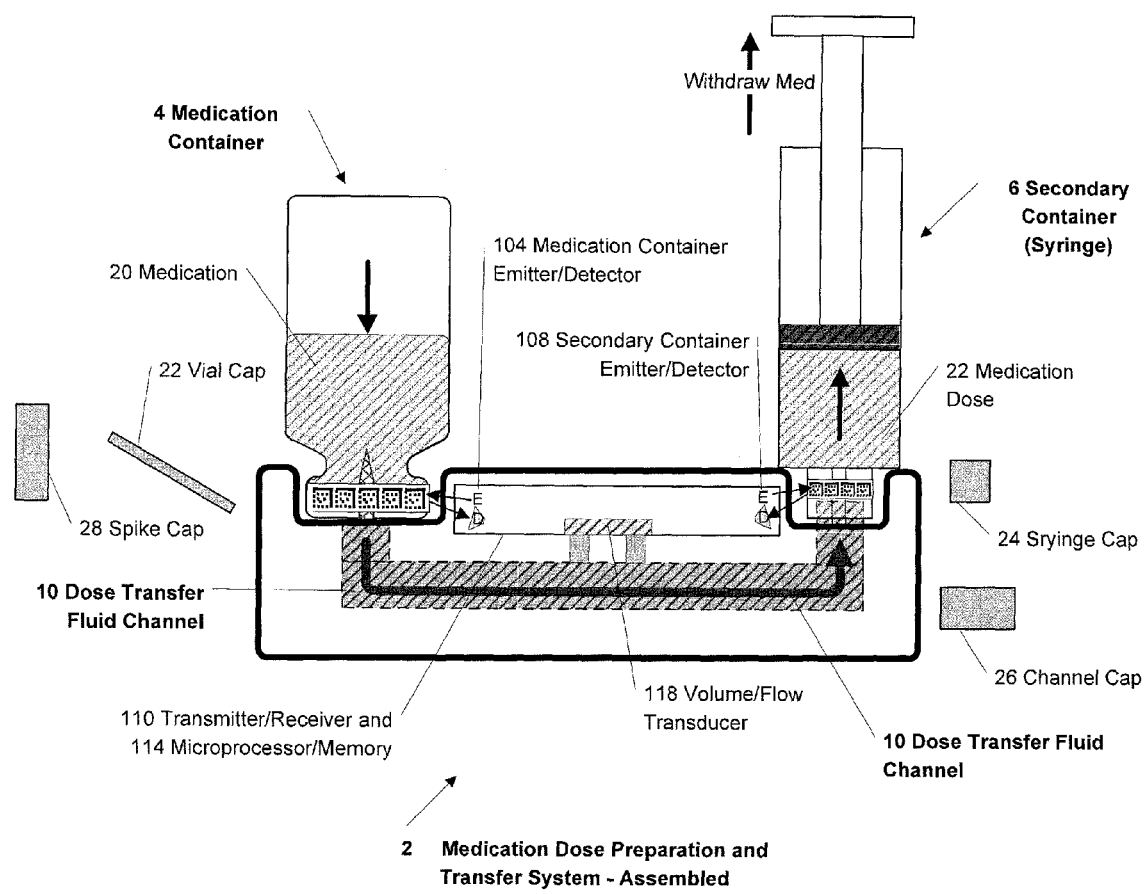
FIG. 8 is a diagram describing the assembly of a medication dose preparation and transfer apparatus with medication containers as in FIG. 7.

FIG. 8 is a diagram illustrating the assembly of a medication dose preparation and transfer apparatus with medication containers as in FIG. 7. Primary medication container 4 and secondary medication container 6 can be prepared for use by removing their respective protective caps 22 and 24. Dose fluid transfer channel 10 can be prepared by removing channel cap 26 and spike cap 28. These caps protect the containers and fluid transfer channel 10 when they are provided sterile (fluid path is sterile). Dose preparation apparatus 8 may be held in a first hand and medication container 4 (vial) is held in a second hand. Fluid channel 10's fluid inlet spike 14 can be inserted through a sterile closure stopper in the vial. Secondly, secondary container 6 can be attached to the fluid channel outlet female lure fitting 15. The other steps of dose preparation and transfer apparatus 8 described in FIG. 6 can be the same.

Figure 9:
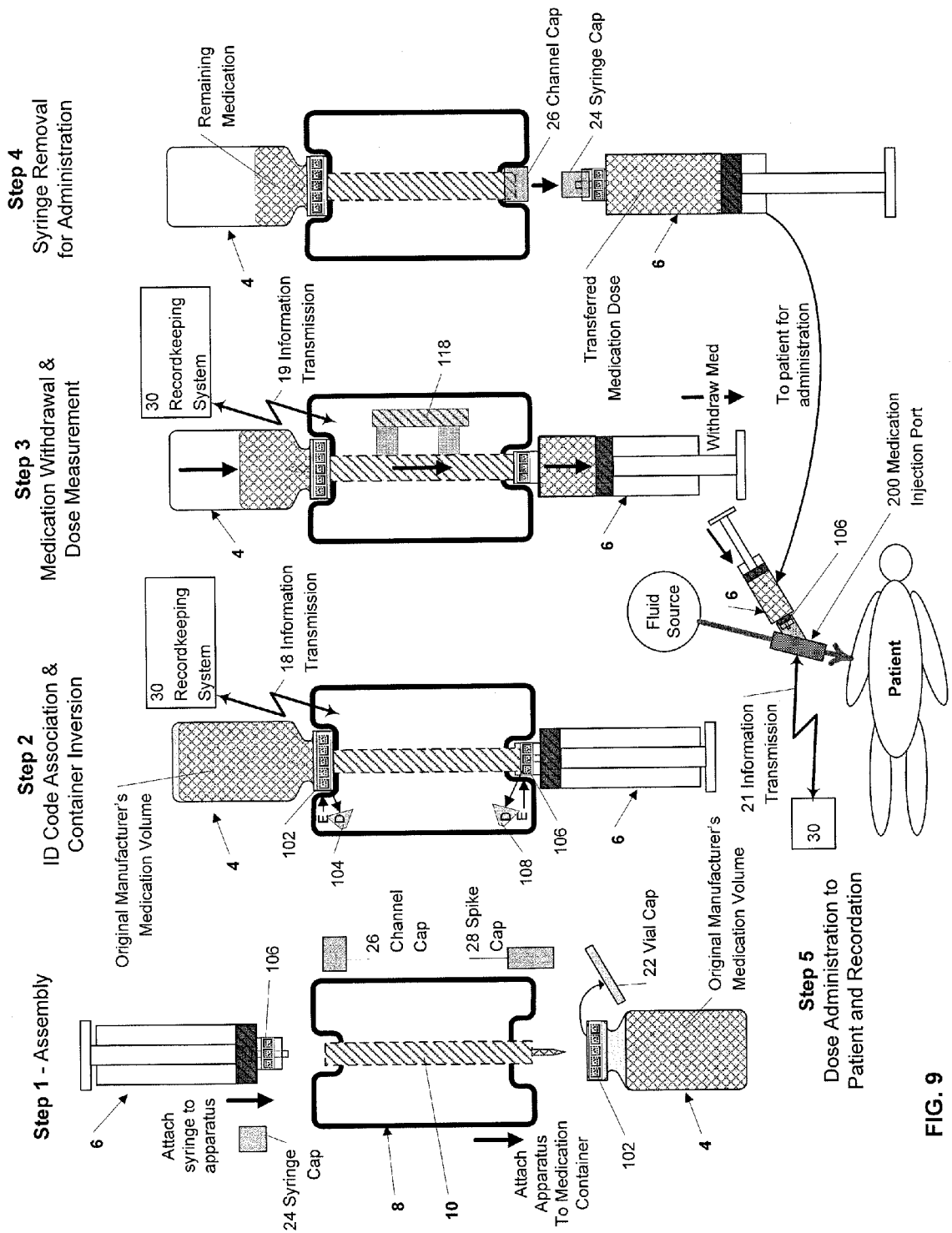
FIG. 9 depicts the basic steps taken in the use of a medication dose preparation and transfer system as in FIG. 3.

FIG. 9 depicts steps that can be taken in the use of a medication dose preparation and transfer system as in FIG. 3.

Step 1: Containers 4 and 6 are prepared for use by removing their protective caps 22 and 24. The dose fluid transfer channel is prepared by removing its caps 26 and 28. Primary container 4 is spiked with the inlet of fluid channel 10 and secondary container 6 is attached to the outlet of fluid channel 10.

Step 2: Connection of containers 4 and 6 allow emitter/detectors 104 and 108 to identify and decode ID Codes 102 and 106 respectively. Information 18 is transmitted to recordkeeping system 30. The two ID Codes can be associated with one another in the recordkeeping system 30, along with an amount of medication transferred between the containers and the volume in each medication container following the transfer. Alternatively, ID Codes 102 and 106 can be associated with one another in dose preparation apparatus 8. The assembled dose preparation and transfer apparatus is inverted allowing withdrawal of medication from vial 4.

Step 3: Medication is withdrawn from container 4 into container 6 by pulling on the plunger rod of the syringe container (6). Volume/flow sensor 118 measures the transferred medication and the dose preparation and transfer apparatus 8 transmits information 19 (volume/flow information) to recordkeeping system 30. The transferred medication dose volume information 19 is associated with ID Code 106 on secondary container 6. The remaining medication in primary container 4 is associated with ID Code 102.

Step 4: Secondary container 6 is detached from fluid channel 10 and protective caps 24 and 26 can be replaced to maintain sterility protection. Syringe 6 is then taken to a patient for dose administration. Alternately, vial 4 and vial spike 14 can be detached from fluid channel 10 and syringe 6 with fluid channel 10 still attached can be used to administer medication to a patient (not shown).

Step 5: A caregiver can then administer the dose from syringe 6 to a patient by attaching it to medication injection port 200 on a fluid administration tubing set. When attached, ID Code 106 is identified by injection port 200 and that information 21 transmitted to recordkeeping system 30. Recordkeeping system 30 associates the injection with the medication withdrawn in Step 3 and medication type and concentration information (ID Code 102) identified in Step 2. The volume of the dose can be measured by injection port 200 and that information 21 can also be transmitted to recordkeeping system 30 for recording in a patient's medication administration record. Information 21 transmitted to recordkeeping system 30 can be integrated or associated with additional information stored within or accessible by recordkeeping systems 30 and utilized to create paper reports and/or electronic records associated with the medication delivery.

The features and functions of medication injection port 200 are described in a medication injection site/medication administration device detailed in the U.S. patent application Ser. Nos. 12/614,276, 12/765,707, and 12/938,300 all entitled "MEDICATION INJECTION SITE AND DATA COLLECTION SYSTEM". Features and functions of a sample vial adapter and encoded fluid transfer element are detailed in U.S. patent application Ser. No. 12/768,509 entitled "MEDICATION AND IDENTIFICATION INFORMATION TRANSFER APPARATUS". The contents of each of the aforementioned applications are hereby fully incorporated by reference. Other medication containers and/or vial adapters and fluid transfer elements may be implemented with this medication dose preparation and transfer system 2. Record keeping system 30 can account for and track medication transfers and administrations to patients in a medication dose history for each patient. Additionally, remaining medication in vial 4 or syringe 6 can be tracked, accounted for and associated with waste disposal. The withdrawn transfer medication volume can be subtracted from the original medication volume in syringe 6 to determine the remaining medication volume. Similarly, the residual medication volume in syringe 6 after dosing and be determined by subtracting the volume of medication delivered to the patient from the total volume of medication that was transferred from vial 4 to syringe 6. The disposed of medication can be tracked by a waste disposal system. For example, a medication wasting device can be configured to receive a syringe 6 containing a controlled substance and bearing an information transfer element ID Code 106 such that the information transfer element is automatically read by the medication wasting device when the syringe is coupled thereto. One example of a medication wasting device is described in U.S. patent application Ser. No. 13/170,073 entitled: "Medication Waste Collection Apparatus", the contents of which are hereby fully incorporated by reference.

Figure 10:
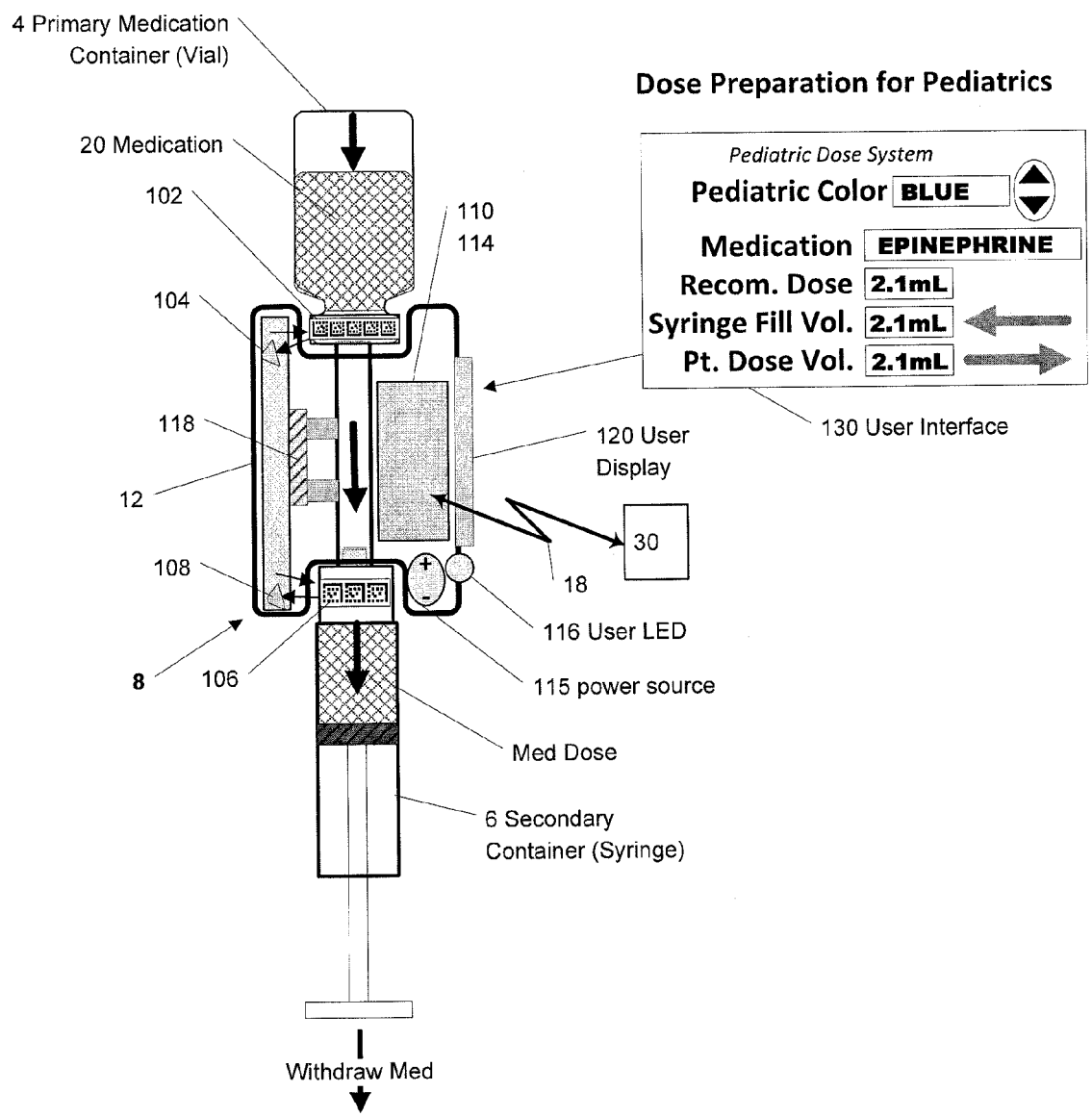
FIG. 10 is a diagram illustrating a medication dose preparation and transfer apparatus as in FIG. 3 with a display.

FIG. 10 is a diagram illustrating a medication dose preparation and transfer apparatus as in FIG. 3 with a display. A display 120 can be included on housing 12 of medication dose preparation and transfer apparatus 8. Display 120 can include a user interface 130 providing information about the fluid transfer process or user guidance to ensure the medication and volume transferred is correct and appropriate for its intended use. For example a pediatric dose preparation system can include the selection of a pediatric color (Broselow color) or patient weight (kilograms or pounds), an indication of the medication type and/or concentration connected identified by ID Code 102 and subsequently recommend a dose or volume for withdrawal from the primary container 4. Pediatric color, patient weight, recommended dose, and other relevant dose preparation parameters can also be downloaded to the medication dose preparation and transfer apparatus 8 from recordkeeping system 30 via information transmission 18. When the secondary container 6 is attached and the syringe plunger rod is pulled a medication dose can be removed from the primary container 4 into secondary container 6. That dose transfer is measured by volume/flow sensor 118 and can be displayed as the syringe fill volume. Subsequently, when the dose is administered to the patient the display can indicate the dose volume. Alternately, the measured volume can be used to calculate a dose in grams, milligrams, micrograms or other medication units instead of milliliters (mL) as shown in FIG. 10.

Information 18 can be bi-directionally exchanged and can include transfer of data from recordkeeping system 30 (including medication management devices and systems, or any healthcare information computer system) to dose preparation and transfer apparatus 8 for display to a user. Information 18 can provide additional data to the display including, but not limited to medication delivery order data, patient-specific identifiers, general or medication-specific dosing limits, data for contraindication checking, Broselow color/classification, patient drug allergies, patient weight, medication data, patient specific data, procedural cautionary data, error prevention data, dose time data, physician instructions, drug manufacturer's instructions, precautions, contraindications, etc.

Figure 11:
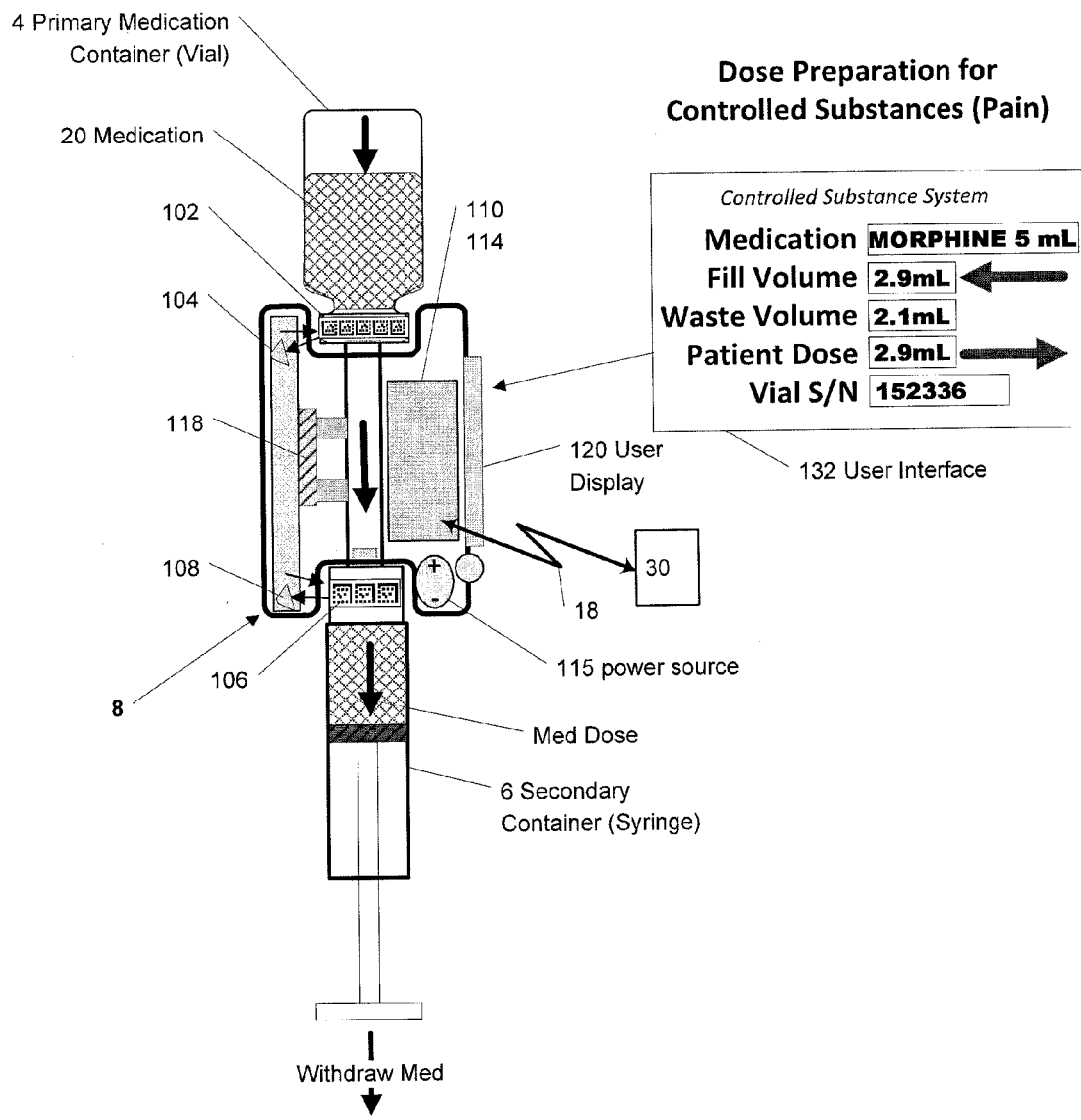
FIG. 11 is a diagram illustrating a second medication dose preparation and transfer apparatus as in FIG. 3 with a display.

FIG. 11 is a diagram illustrating a second medication dose preparation and transfer apparatus as in FIG. 3 with a display. A display 120 can be included on housing 12 of medication dose preparation and transfer apparatus 8. Display 120 can include a user interface 130 providing information about the fluid transfer process or user guidance to ensure the medication and volume transferred is correct and appropriate for its intended use. For example a controlled substance dose preparation system can include an indication of the medication type and or concentration connected identified by ID Code 102. A caregiver can determine an appropriate dose volume and withdraw that dose volume from the primary container 4. When the secondary container 6 is attached and the syringe plunger rod is pulled a medication dose is removed from the primary container 4 into secondary container 6. That dose transfer is measured by volume/flow sensor 118 and can be displayed as the syringe fill volume. Subsequently, when the dose is administered to the patient the display can indicate the patient dose volume.

Alternately, the entire volume of medication can be withdrawn from vial 4. In this case any extra medication can be disposed of in a waste container prior to dose administration to a patient. In this case the remaining volume is retained in syringe 6 for administration to the patient. Information 18 about the medication (ID Code 102, the withdrawn volume, the disposed of waste volume measured, the unique syringe ID Code 106) can all be transferred to recordkeeping system 30 for tracking and accounting of controlled substances. Dose volumes can be used to calculate a dose in grams, milligrams, micrograms or other medication units instead of milliliters (mL) as shown in FIG. 11.

Figure 12:
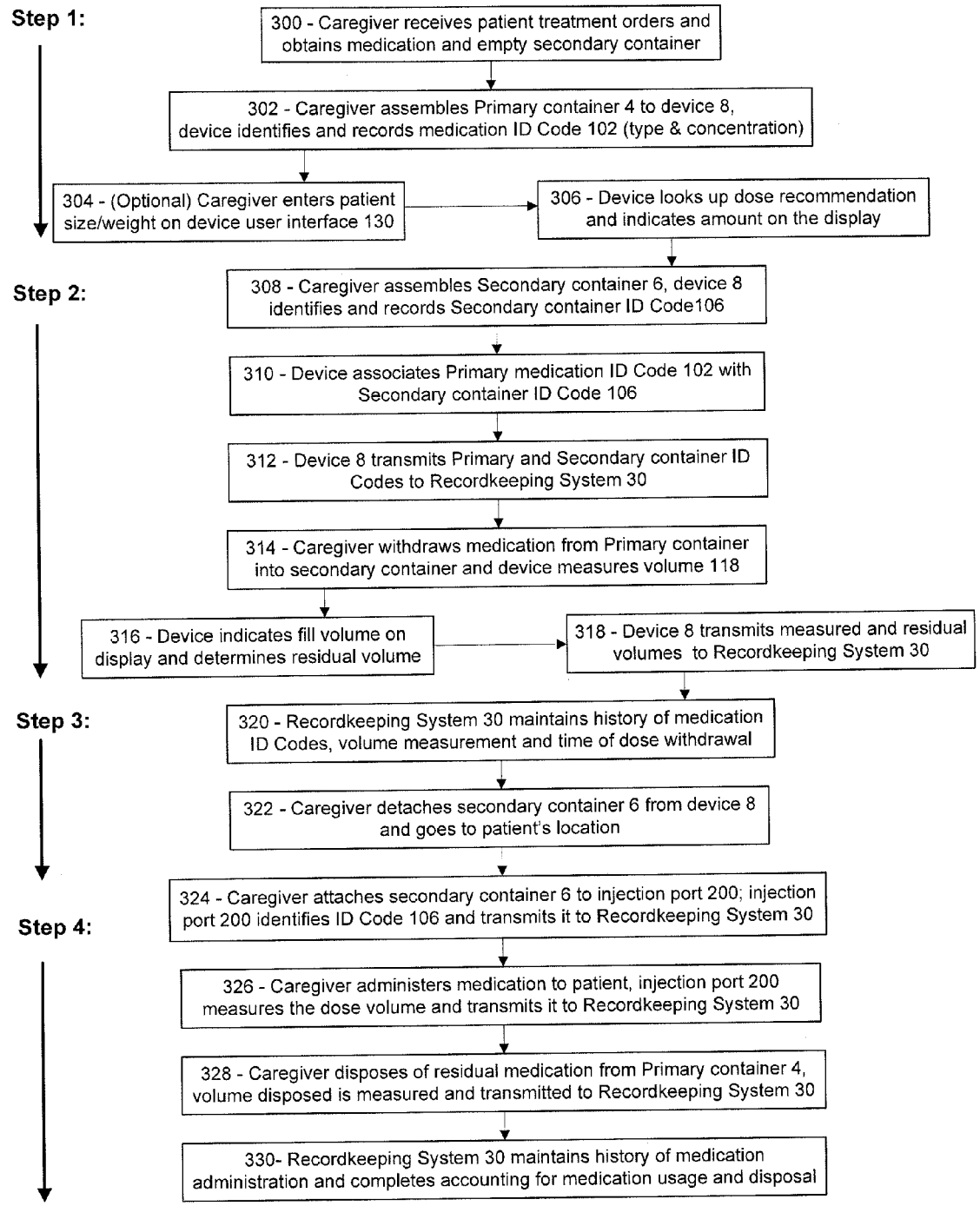
FIG. 12 is a diagram showing the sequence of operation for the device in FIG. 11.

FIG. 12 is a diagram showing an example sequence of operation for the device in FIG. 11.

Step 1: A caregiver receives medication orders and prepares the dose preparation and transfer apparatus 8 (300, 302, 304, 306).

Step 2: A caregiver assembles the medication containers (4 and 6) to medication dose preparation and transfer apparatus 8 (308, 310, 312, 314, 316, 318).

Step 3: The recordkeeping system 30 maintains a tracking record of ID codes and transfer volumes (320) and the caregiver detaches the secondary container 6 from apparatus 8 (322).

Step 4: The caregiver administers the medication to the patient and disposes of unused medication waste (324, 326, 328). The recordkeeping system 30 accounts for the history of medication transferred with from primary medication container 4 to secondary medication container 6, the dose administered to the patient, and any residual waste disposal (330).

Figure 13:
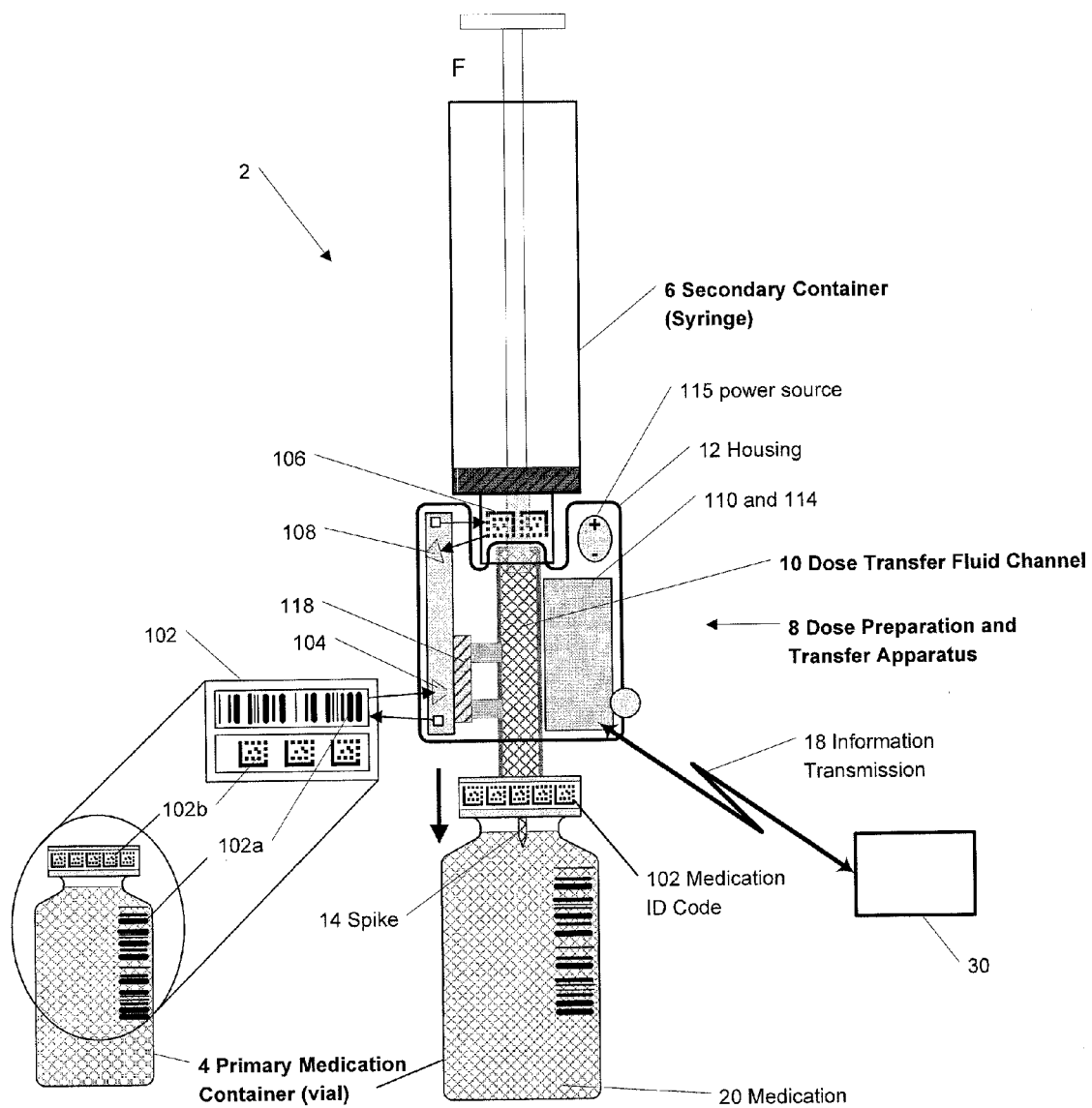
FIG. 13 is a diagram describing a detailed view of a sixth medication dose preparation and transfer system as in FIG. 1.

FIG. 13 is a diagram describing a detailed view of a sixth medication dose preparation and transfer system 2 as in FIG. 1. In this implementation, medication ID Code 102 can be placed on the primary medication container vial 4 (102a) or on vial closure rim (102b) of the primary medication container 4. In FIG. 13, medication container emitter/detector 104 can identify medication ID Code 102 (102a or 102b) on primary medication container (vial) 4 when it is not attached to dose transfer fluid channel 10. Then, after ID Code 102 has been identified by dose preparation and transfer apparatus 8 it can be spiked or attached onto fluid channel 10, inverted and prepared for dose transfer into secondary container 6. Secondary container 6 can still have ID Code 106 located at the fluid outlet and can be identified by emitter/detector 108. In this implementation dose transfer fluid channel 10 couples primary medication container 4 to secondary container 6. Housing 12 can contain a volume/flow transducer 118 coupled to dose transfer fluid channel 10 to measure an amount of medication transferred from vial 4 to syringe 6. The other features and functions of dose preparation and transfer apparatus 8 described in FIG. 3 can be the same.

Figure 14:
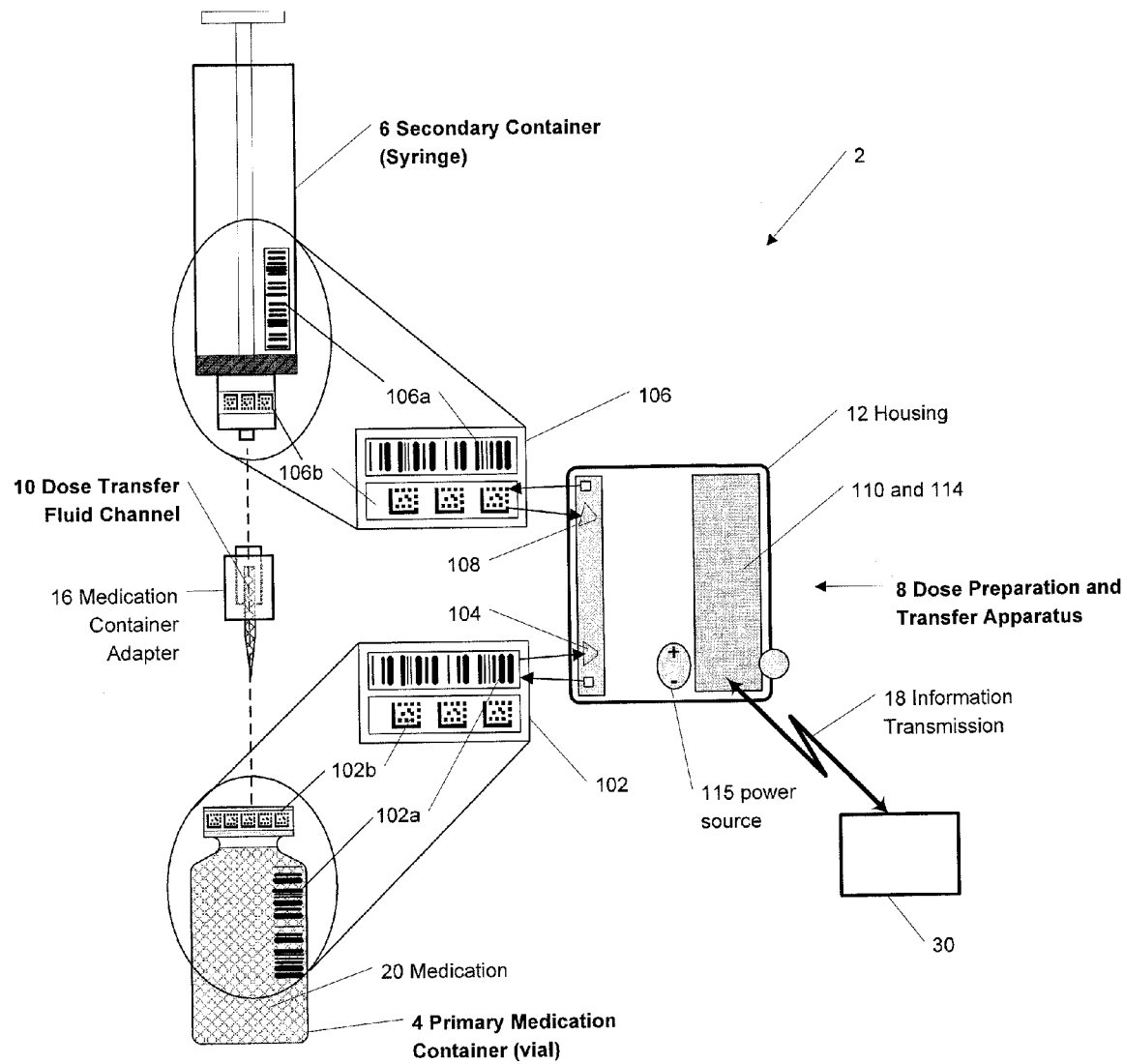
FIG. 14 is a diagram describing a detailed view of a seventh medication dose preparation and transfer system as in FIG. 1.

FIG. 14 is a diagram describing a detailed view of a seventh medication dose preparation and transfer system 2 as in FIG. 1. In this implementation, dose preparation and transfer apparatus 8 does not utilize dose transfer fluid channel 10 and instead uses a separate vial adapter 16. Housing 12 can contain identification emitter/detectors 104 and 108 to read ID Codes 102 and 106 respectively. Housing 12 can contain hardware and software elements 110 and 114 to process and transmit or receive information 18 to/from recordkeeping system 30.

ID Code 102 can be placed on the primary medication container vial 4 (102a) or on vial closure rim (102b) of the primary medication container 4 as in FIG. 13. Additionally, ID Code 106 can be placed on secondary medication container 6 (106a) or on the syringe fluid outlet (106b) of secondary medication container 6. Emitter/detector 104 can identify ID Code 102 (102a or 102b) on primary medication container (vial) 4 when it is not attached to dose transfer fluid channel 10. Emitter/detector 108 can identify ID Code 106 (106a or 106b) on secondary medication container (syringe) 6 when it is not attached to dose transfer fluid channel 10.

Then, after ID Codes 102 and 104 have been identified by dose preparation and transfer apparatus 8 they can be associated with each other via information transmission 18 using recordkeeping system 30.

When used, primary medication container (vial) 4 is coupled to secondary container (syringe) 6 for fluid transfer. Vial 4 can be coupled (spiked) using medication container adapter 16 attached to the fluid outlet of secondary container (syringe) 6. Adapter 16 can contain dose transfer fluid channel 10. Adapter 16 can be a vial adapter, a needle, a blunt tip cannula, a needle-less luer adapter with spike as shown in FIG. 2 or any fluid transfer apparatus designed to transfer medication 20 from vial 4 into syringe 6.

Following the coupling of vial 4 to syringe 6 through dose transfer fluid channel 10, the assembly is inverted and prepared for dose transfer. In this implementation dose transfer fluid channel 10 couples primary medication container 4 to secondary container 6. Measurement of fluid transfer is done by the caregiver and manually entered into recordkeeping system 30. The other features and functions of dose preparation and transfer apparatus 8 described in FIG. 2 can be the same.

The subject matter described herein can be embodied in systems, apparatus, methods, and/or articles depending on the desired configuration. In particular, aspects of the subject matter described herein can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications, applications, components, or code) include machine instructions for a programmable processor, and can be implemented in a high-level procedural and/or object-oriented programming language, and/or in assembly/machine language. As used herein, the term "machine-readable medium" refers to any non-transitory computer program product, apparatus and/or device (e.g., magnetic discs, optical disks, memory, Programmable Logic Devices (PLDs)) used to provide machine instructions and/or data to a programmable processor. The term "machine-readable signal" refers to any signal used to provide machine instructions and/or data to a programmable processor.

The user interface can include, for example a cathode ray tube (CRT) or a liquid crystal display (LCD) monitor for displaying information to the user. The user may input any information to the display device using a keyboard and a pointing device, such as for example a mouse or a trackball. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like. Other kinds of devices can be used to provide for interaction with a user as well. Further, the input from the user may be received in any form, including, but not limited to, acoustic, speech, or tactile input.

Besides a digital feedback shown to the health care provider, the feedback may be an audio signal, a video signal, or any form of sensory feedback such as a visual feedback, an auditory feedback, or tactile feedback.

The implementations set forth in the foregoing description do not represent all implementations consistent with the subject matter described herein. Instead, they are merely some examples consistent with aspects related to the described subject matter. Wherever possible, the same reference numbers will be used throughout the drawings to refer to the same or like parts.

Although a few variations have been described in detail above, other modifications or additions are possible. In particular, further features and/or variations can be provided in addition to those set forth herein. For example, the implementations described above can be directed to various combinations and sub-combinations of the disclosed features and/or combinations and sub-combinations of several further features disclosed above. In addition, the logic flows and steps for use described herein do not require the particular order shown, or sequential order, to achieve desirable results. Other embodiments can be within the scope of the claim.

What is claimed is:

1. An apparatus for transferring medication from a primary medication container to a manually injectable secondary medication container comprising:
   a fluid channel disposed in a housing that terminates at a primary medication container port on a first end and a secondary medication container port on a second end;
   a primary medication container coupling configured to fluidically couple the primary medication container to the primary medication container port;
   a secondary medication container coupling configured to fluidically couple the secondary medication container to the secondary medication container port;
   at least one identification sensor disposed in the housing adjacent to at least one of the primary medication container port or the secondary medication container port configured to sense (i) an information transfer element on the primary medication container and (ii) an information transfer element on the secondary medication container, the information transfer element on the primary container being used to characterize the medication; and
   a communications module to transmit data obtained by and/or derived from the at least one identification sensor to a remote computing system to enable the remote computing system to associate data characterizing the medication with the secondary medication container.

2. An apparatus as in claim 1, wherein the primary medication container coupling comprises a spike to penetrate a barrier of the primary medication container.

3. An apparatus as in claim 1, wherein the secondary medication container coupling comprises a female luer fitting to mate with a male luer fitting of the secondary medication container.

4. An apparatus as in claim 1, wherein the primary medication container is a vial and the apparatus further comprises a vial adapter having the information transfer element disposed thereon.

5. An apparatus as in claim 1, wherein the secondary medication container is a syringe and the information transfer element is disposed upon an encoded hub attached to a fluid outlet of the syringe that is configured to fluidically couple with the secondary medication container port.

6. An apparatus as in claim 1, wherein the communications module wirelessly transmits data to and/or receives data from the remote computing system.

7. An apparatus as in claim 1, wherein a first identification sensor senses the information transfer element of a primary medication container and a second identification sensor senses the information transfer element of the secondary medication container.

8. An apparatus as in claim 1, wherein the information transfer element on at least one of the primary medication container and the secondary medication container comprises a unique identifier.

9. An apparatus in claim 8, wherein the unique identifier is a serial number.

10. An apparatus as in claim 1, further comprising:
    at least one flow sensor to characterize an amount of medication passing through the fluid channel;
    wherein the communications module further transmits data characterizing the amount of medication passing through the fluid channel.

11. An apparatus as in claim 10, wherein the at least one flow sensor comprises a bi-directional flow sensor measuring fluid flow in two opposing directions; and
    wherein transmitted data separately characterizes fluid flow in both opposing directions.

12. An apparatus as in claim 1, further comprising:
    memory for storing data obtained from the at least one identification sensor; and
    at least one data processor for processing data stored in the memory.

13. An apparatus as in claim 10, further comprising:
    memory for storing data obtained from the at least one identification sensor and the at least one flow sensor; and
    at least one data processor for processing data stored in the memory.

14. An apparatus as in claim 1, further comprising:
    a user indicator providing visual and/or audio feedback to a user of the apparatus.

15. An apparatus as in claim 14, wherein the feedback is selected from a group consisting of: medication name, medication category, recommended dosage, secondary medication container fill volume, medication waste volume, secondary medication container identifier, and partial dosage volume.

16. An apparatus as in claim 1, wherein the fluid channel is selectively removable to avoid medication cross-contamination and/or sterility issues.

17. An apparatus as in claim 1, wherein the housing comprises a reusable sub-housing and a disposable sub-housing, the reusable sub-housing being operatively coupled to the disposable sub-housing, wherein the reusable sub-housing is intended for use by a plurality of patients and the disposable sub-housing is intended for use by a single patient.

18. An apparatus as in claim 17, wherein the fluid channel is disposed within the disposable sub-housing.

19. An apparatus as in claim 18, wherein the disposable sub-housing forms part of a kit including a sterile pouch enveloping the disposable sub-housing.

20. An apparatus as in claim 18, further comprising:
    memory within the disposable sub-housing for storing data comprising: calibration information and/or a serial number or a unique identification number.

21. An apparatus as in claim 1, wherein the remote computing system is selected from a group consisting of: medication management devices and systems, electronic medical records systems, pharmacy management and fulfillment systems, medication storage systems, medication dispensing stations, and medication waste disposal systems.

22. An apparatus as in claim 1, wherein the fluid channel is linear.

23. An apparatus as in claim 1, further comprising:
removable channel caps secured to the primary medication container port and the secondary medication container port.

24. An apparatus as in claim 1, wherein the housing has a size and shape to allow a user to hold the housing and a primary medication container in a first hand and to operate the manually injectable secondary medication container using a second hand.

25. An apparatus as in claim 1, further comprising:
a display disposed on the housing;
wherein the communications module receives data from at least one computing system characterizing the medication, at least a portion of the received data being displayed on the display.

26. An apparatus as in claim 25, wherein at least a portion of the information being displayed includes one or more of: information about the fluid transfer process, user guidance, information about the dose to be administered, information about the dose administered to a patient, and patient specific medication administration guidelines or restrictions.

27. An apparatus as in claim 26, wherein the received data is selected from a group consisting of: medication delivery order data, patient-specific identifiers, general or medication-specific dosing limits, data for contraindication checking, Broselow color/classification, patient drug allergies, patient weight, medication data, patient specific data, procedural cautionary data, error prevention data, dose time data, physician instructions, drug manufacturer instructions, precautions associated with the medication, and contraindications associated with the medication.

28. An apparatus as in claim 1, wherein the at least one identification sensor detects the information transfer element using one or more technologies selected from a group consisting of: optical, magnetic, mechanical, conductive, capacitive, inductive, proximity sensors, infrared, and switchable RFID.

29. A system comprising:
a primary medication container;
a manually injectable secondary medication container; and
a dose preparation and transfer apparatus comprising:
a fluid channel disposed in a housing that terminates at a primary medication container port on a first end and a secondary medication container port on a second end;
a primary medication container coupling configured to fluidically couple the primary medication container to the primary medication container port;
a secondary medication container coupling configured to fluidically couple the secondary medication container to the secondary medication container port;
at least one identification sensor disposed in the housing adjacent to at least one of the primary medication container port or the secondary medication container port that is configured to sense (i) an information transfer element on the primary medication container and (ii) an information transfer element on the secondary medication container, the information transfer element on the primary container being used to characterize the medication; and
a communications module to transmit data obtained by and/or derived from the at least one identification sensor to a remote computing system to enable the remote computing system to associate data characterizing the medication with the secondary medication container.

30. A method comprising:
detecting, by a dose preparation and transfer apparatus, an information transfer element on a primary medication container;
detecting, by the dose preparation and transfer apparatus, an information transfer element on a secondary medication container; and
transmitting, by the dose preparation and transfer apparatus, to a remote computing system, data characterizing the detected information transfer elements;
wherein the dose preparation and transfer apparatus comprises:
a fluid channel disposed in a housing that terminates at a primary medication container port on a first end and a secondary medication container port on a second end;
a primary medication container coupling configured to fluidically couple the primary medication container to the primary medication container port;
a secondary medication container coupling configured to fluidically couple the secondary medication container to the secondary medication container port;
at least one identification sensor disposed in the housing adjacent to at least one of the primary medication container port or the secondary medication container port configured to sense (i) an information transfer element on the primary medication container and (ii) an information transfer element on the secondary medication container, the information transfer element on the primary container being used to characterize the medication; and
a communications module to transmit data obtained by and/or derived from the at least one identification sensor to a remote computing system to enable the remote computing system to associate data characterizing the medication with the secondary medication container.

31. A method comprising:
detecting, by a dose preparation and transfer apparatus, an information transfer element on a primary medication container;
detecting, by the dose preparation and transfer apparatus, an information transfer element on a secondary medication container;
detecting, by the dose preparation and transfer apparatus, an amount of medication transferred from the primary container to the secondary container;
transmitting, by the dose preparation and transfer apparatus to a remote computing system, data characterizing the detected primary medication information transfer element, the detected secondary medication container information transfer element and the detected amount of medication transferred;
wherein the dose preparation and transfer apparatus comprises:
a fluid channel disposed in a housing that terminates at a primary medication container port on a first end and a secondary medication container port on a second end;
a primary medication container coupling configured to fluidically couple the primary medication container to the primary medication container port;
a secondary medication container coupling configured to fluidically couple the secondary medication container to the secondary medication container port;
at least one identification sensor disposed in the housing adjacent to at least one of the primary medication container port or the secondary medication container port that is configured to sense (i) an information transfer element on the primary medication container and (ii) an information transfer element on the secondary medication container, the information transfer element on the primary container being used to characterize the medication;

a flow sensor to characterize an amount of medication passing through the fluid channel; and a communications module to transmit data obtained by the at least one identification sensor and flow sensor to a remote computing system to enable the remote computing system to associate data characterizing the medication with the secondary medication container.

32. An apparatus comprising:

a fluid channel disposed in a housing that terminates at a primary medication container port on a first end and a secondary medication container port on a second end;

a primary medication container coupling configured to fluidically couple the primary medication container to the primary medication container port;

a secondary medication container coupling configured to fluidically couple the secondary medication container to the secondary medication container port;

identification means disposed in the housing adjacent to at least one of the primary medication container port or the secondary medication container port configured to sense (i) an information transfer element on the primary medication container and (ii) an information transfer element on the secondary medication container, the information transfer element on the primary container being used to characterize the medication; and a communications module to transmit data obtained by and/or derived from the identification means to a remote computing system to enable the remote computing system to associate data characterizing the medication with the secondary medication container.

\* \* \* \* \*